United States Patent
van Nieuw Amerongen et al.

(10) Patent No.: US 9,290,765 B2
(45) Date of Patent: Mar. 22, 2016

(54) PROTECTION AGAINST ENDOTHELIAL BARRIER DYSFUNCTION THROUGH INHIBITION OF THE TYROSINE KINASE ABL-RELATED GENE (ARG)

(75) Inventors: Geerten P. van Nieuw Amerongen, Amsterdam (NL); Anton Vonk Noordegraaf, Amsterdam (NL); Jurjan Aman, Amsterdam (NL); Victor W. M. van Hinsbergh, Amsterdam (NL)

(73) Assignee: VERENIGING VOOR CHRISTELIJK HOGER ONDERWIJS, WETENSCHAPPELIJK ONDERZOEK EN PATIËNTENZORG, Amsterdam (NL)

( * ) Notice: Subject to any disclaimer, the term of this patent is extended or adjusted under 35 U.S.C. 154(b) by 0 days.

(21) Appl. No.: 14/115,279

(22) PCT Filed: May 2, 2011

(86) PCT No.: PCT/NL2011/050299
§ 371 (c)(1),
(2), (4) Date: Mar. 17, 2014

(87) PCT Pub. No.: WO2012/150857
PCT Pub. Date: Nov. 8, 2012

(65) Prior Publication Data
US 2014/0187605 A1    Jul. 3, 2014

(51) Int. Cl.
| | |
|---|---|
| *A61K 48/00* | (2006.01) |
| *C12N 15/113* | (2010.01) |
| *A61K 31/713* | (2006.01) |
| *A61K 31/506* | (2006.01) |

(52) U.S. Cl.
CPC .......... *C12N 15/1135* (2013.01); *A61K 31/506* (2013.01); *A61K 31/713* (2013.01); *C12N 15/1137* (2013.01); *C12N 2310/14* (2013.01)

(58) Field of Classification Search
None
See application file for complete search history.

(56) References Cited

U.S. PATENT DOCUMENTS

| | | |
|---|---|---|
| 5,521,184 A | 5/1996 | Zimmermann et al. |
| 6,596,746 B1 | 7/2003 | Das et al. |
| 7,169,791 B2 | 1/2007 | Breitenstein et al. |
| 2005/0075492 A1 | 4/2005 | Chen et al. |
| 2005/0246791 A1 | 11/2005 | Chang et al. |
| 2010/0234451 A1 | 9/2010 | Worm |
| 2010/0292310 A1 | 11/2010 | Kelley et al. |
| 2011/0092572 A1 | 4/2011 | Tachas et al. |

FOREIGN PATENT DOCUMENTS

WO    2012150857 A1    11/2012

OTHER PUBLICATIONS

PCT International Search Report, PCT/NL2011/050299 dated Dec. 14, 2011.
Van Nieuw et al., Involvement of Rho Kinase in Endothelial Barrier Maintenance, Arteriosclerosis, Thrombosis, and Vascular Biology, Jan. 1, 2007, pp. 2332-2339, vol. 27, No. 11.
Wang et al., Calcium/Calmodulin-dependent Protein Kinase II Delta 6 (CaMKii 6) and RhoA Involvement in Thrombin-induced Endothelial Barrier Dysfunction, Jounral of Biological Chemistry, Jul. 9, 2010, pp. 21303-21312, vol. 285, No. 28.
Birukova et al., Atrial natriuretic peptide attenuates LPS-induced lung vascular leak: role of PAK1, American Journal of Physiology, Lung Cellular and Molecular Physiology, Nov. 1, 2010, pp. 652-663, vol. 299, No. 5.
Van Nieuw Amerongen et al., Targets for pharmacological intervention of endothelial hyperpermeability and barrier function, Vascular Pharmacology, Nov. 1, 2002, pp. 257-272, vol. 39, No. 4-5, Elsevier, Amsterdam, NL.
Su et al., Activation of PDGF-CC by Tissue Plasminogen Activator Impairs Blood Brain Barrier Integrity During Ischemic Stroke, Nat. Med., Jul. 2008, pp. 731-737, vol. 14, No. 7.
Armulik et al., Pericytes regulate the blood-brain barrier, Nature, Nov. 25, 2010, p. 557-562, vol. 468, Macmillan Publishers Limited.

*Primary Examiner* — Kimberly Chong
(74) *Attorney, Agent, or Firm* — TraskBritt, P.C.

(57) ABSTRACT

The invention relates to the field of endothelial barrier dysfunction, particular, the invention relates to new methods for the treatment of endothelial barrier dysfunction, such as inflammatory edema by inhibiting Abl-related gene (ARG).

23 Claims, 11 Drawing Sheets

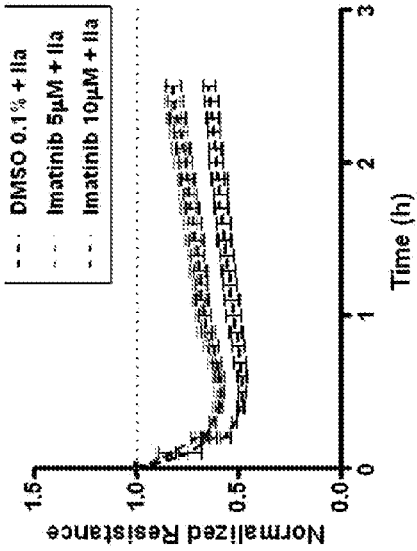
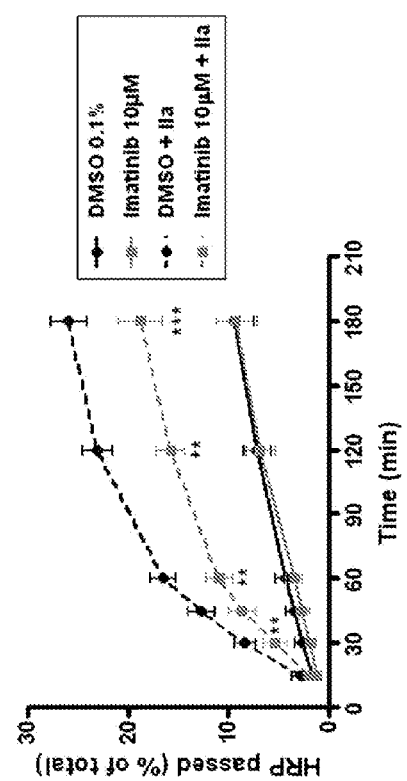
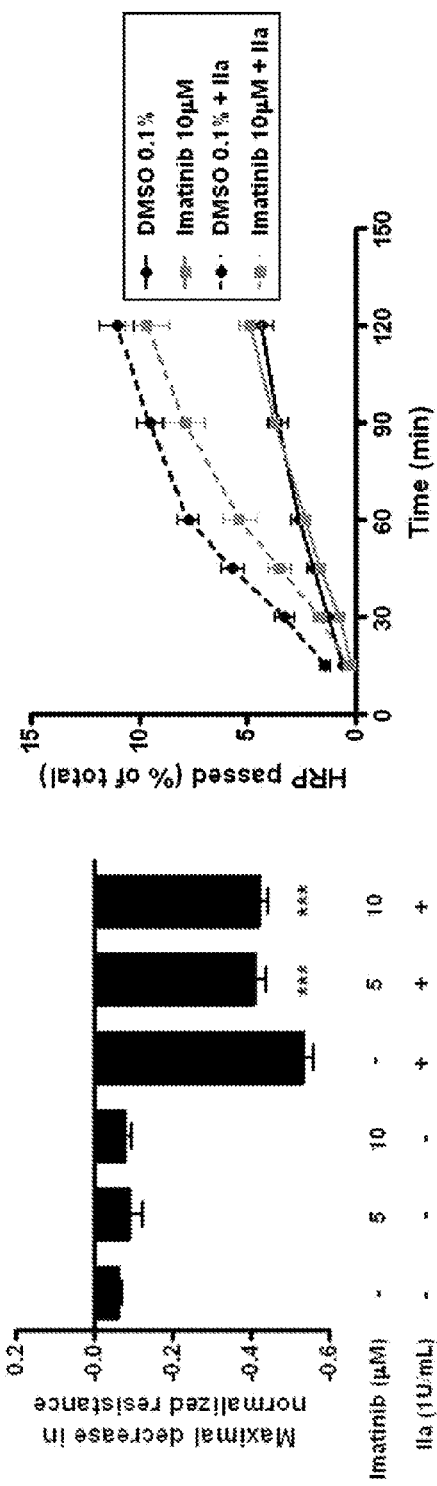

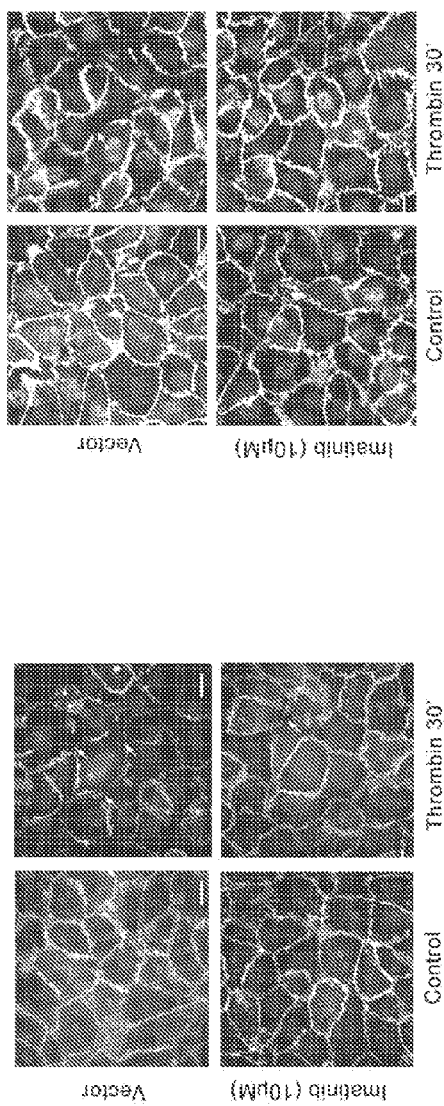
Fig. 1E
Fig. 1F
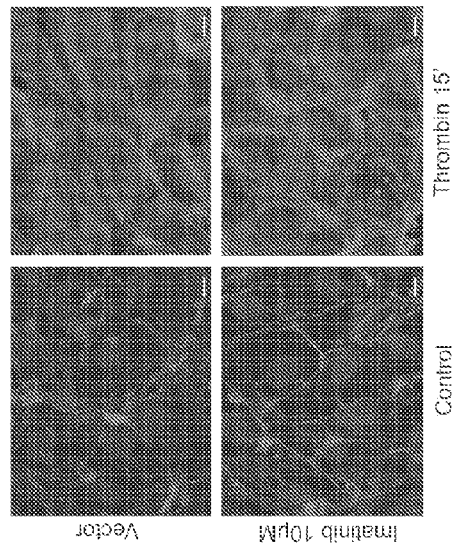
Fig. 2A

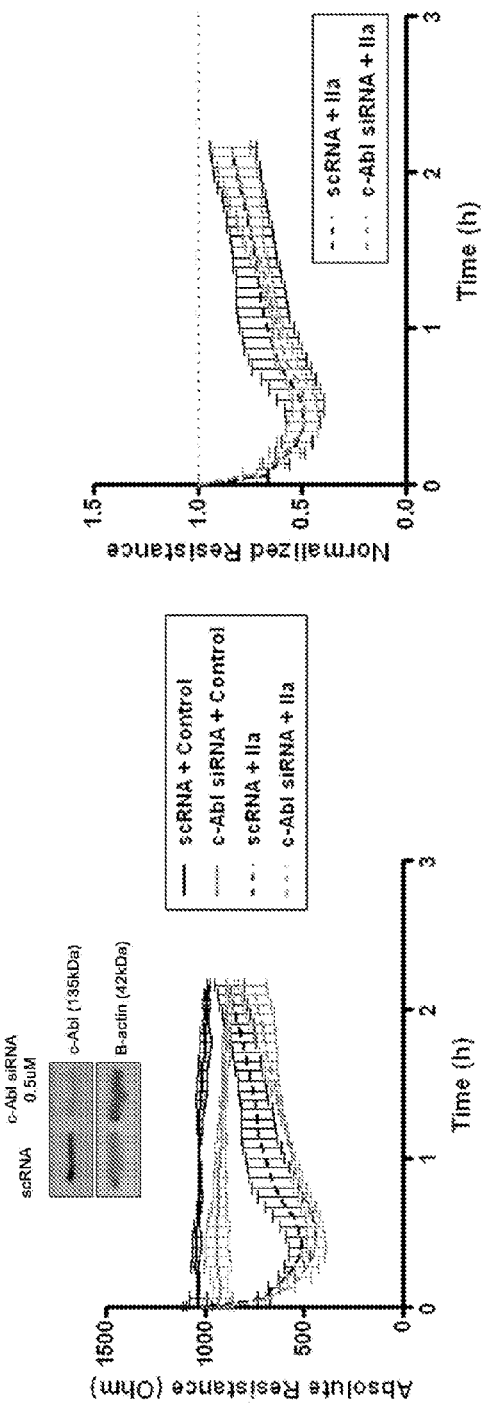
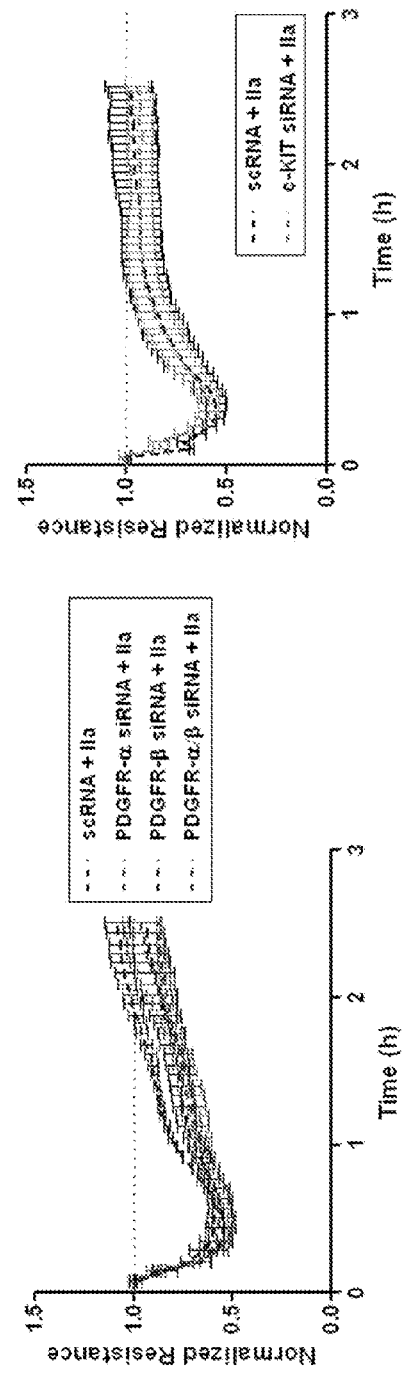
Fig. 3A
Fig. 3B
Fig. 3C
Fig. 3D

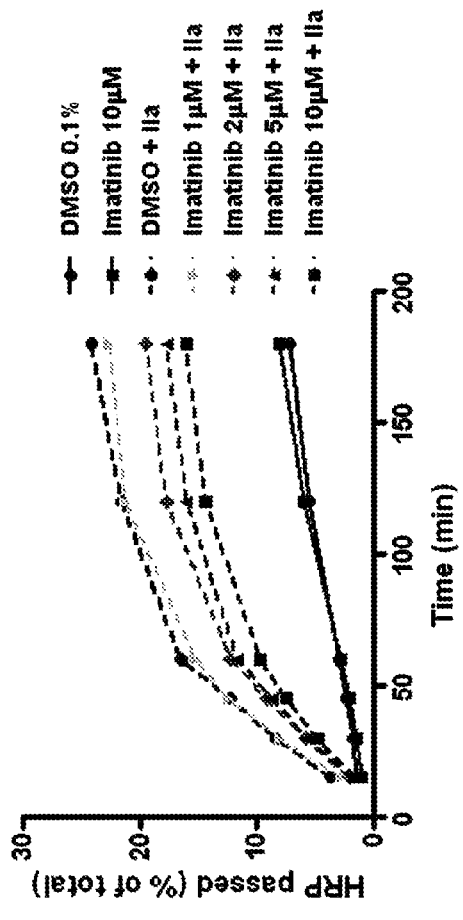
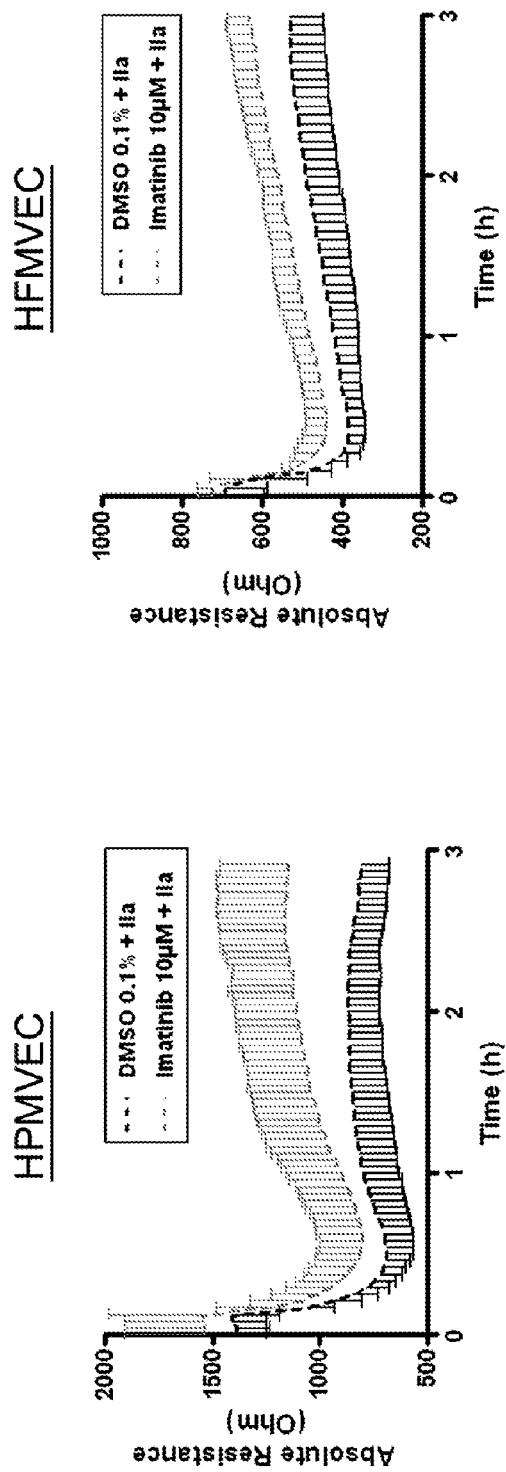
Fig. 5A
Fig. 5B
Fig. 5C

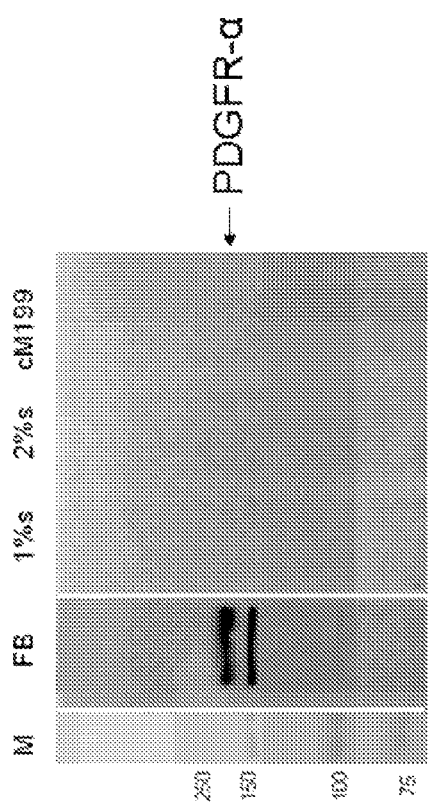
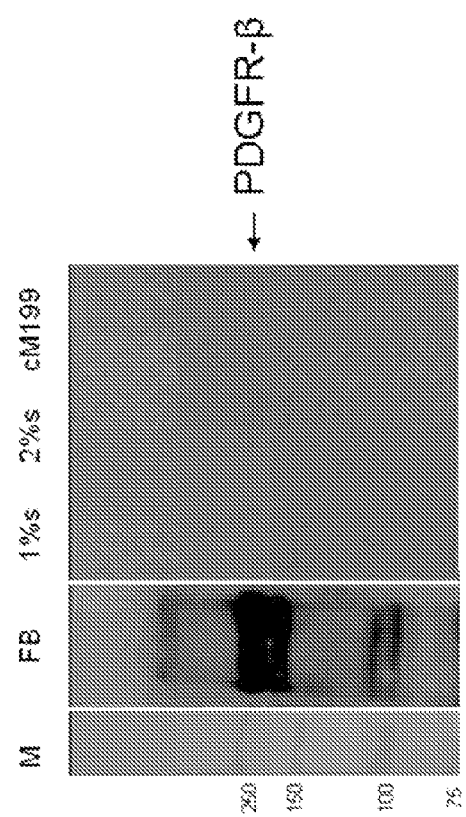
Fig. 7E
Fig. 7F

PROTECTION AGAINST ENDOTHELIAL BARRIER DYSFUNCTION THROUGH INHIBITION OF THE TYROSINE KINASE ABL-RELATED GENE (ARG)

The invention relates to the field of endothelial barrier dysfunction. In particular, the invention relates to new methods for the treatment of syndromes/diseases characterized by endothelial barrier dysfunction, such as inflammatory edema.

Abl protein non-receptor tyrosine kinases are involved in the regulation of a number of cell processes including proliferation, survival, and migration. There are two Abl family members in mammals: c-Abl (Abl 1) and Abl related gene (ARG) also known as Abl 2 (Kruh, et al. Science December 1986: 1545-1548). The tyrosine kinase domains of c-Abl and ARG are 94% identical, however their similarity diverges at the C-terminus. While both c-Abl and ARG contain a calponin-homology F-actin binding domain, c-Abl has a DNA binding domain and a G-actin binding domain and ARG additionally contains a talin-like F-actin binding domain and a microtubule binding domain.

ARG has been implicated in affecting cytoskeleton processes. For example, ARG activation leads to actin polymerization and F-actin filament formation through F-actin bundling.[32,33] Moreover, ARG regulates the actin filament structure by ARG-dependent phosphorylation of the actin-adapting proteins cortactin[34] and N-WASp.[35] The involvement of ARG in cytoskeleton regulation yields an important role for ARG in cell movements like migration, cell contraction, lamellipodia formation etc. The exact function of ARG in these processes may depend on the spatial distribution and temporal regulation of ARG activity.

c-Abl is best known for its role as a proto-oncogene. The fusion of Bcr and c-Abl genes results in a chimeric Bcr-Abl protein having constitutively activated Abl tyrosine kinase activity. (Lugo et al., Science 1990, 247:1079-1082). Bcr-Abl is the underlying cause of chronic myeloid leukemia. One of the treatments for Brc-Abl positive leukaemia,[5-7] is the use of imatinib. Imatinib is a small molecule inhibitor that blocks the ATPase activity of c-Abl as well as ARG, PDGFR and c-KIT.[4]

c-Abl is also involved in regulating endothelial barrier function by phosphorylating nonmuscle myosin light chain kinase. Endothelial barrier dysfunction is involved in the pathophysiology of a wide variety of diseases. As the endothelium tightly controls the flux of fluid from the circulation to the surrounding tissues, dysfunction of this barrier in a pathological state (e.g. inflammation) leads to uncontrolled fluid extravasation and edema.[1,2] If vital organs are involved, edema may lead to organ failure with consequent morbidity and mortality.

siRNA against c-Abl resulted in a decrease in endothelial cell barrier integrity after treatment with a barrier-enhancing agonist, i.e, sphingosine 1-phosphate (Dudek et al. Mol Bio Cell 2010 21:4042-4056). The effect of inhibition of c-Abl on disrupting endothelial cell barrier integrity is also supported by one of the side effects of long-term treatment with imatinib, namely edema.[7]

In contrast to studies reporting subcutaneous edema as a consequence of chronic imatinib treatment, the present disclosure demonstrates that short-term treatment with imatinib protects against endothelial barrier dysfunction. FIG. 1A-D demonstrates that short-term treatment of imatinib attenuates thrombin-induced endothelial hypermeability. Imatinib exerts these effects by preservation of adherence junction (AJ) integrity and cell-cell adhesion (FIG. 1E-F). Considering previous reports on subcutaneous edema as a side effect[7] of imatinib treatment, it is also important to note that in the concentrations used in the study, imatinib did not affect basal endothelial barrier integrity. These findings suggest that the subcutaneous edema as a side-effect of imatinib treatment most likely results from chronic PDGFR inhibition in pericytes and consequent disturbed vascular support.

Thrombin-induced adherence junction dissociation and loss of cell-cell adhesion involves $Ca^{2+}$ and RhoA/Rho kinase mediated actin-myosin contraction.[2,24] Since most imatinib-sensitive kinases (c-Abl[25], PDGFR[26] and Arg[27,28]) have been reported to affect Rho kinase activity, we hypothesized that imatinib attenuates the thrombin-induced changes in actin cytoskeleton via inhibition of the RhoA/Rho kinase pathway. Surprisingly, the endothelial cell barrier protective effect of imatinib was independent of the RhoA/Rho kinase pathway (FIG. 2B-E).

As imatinib was primarily developed to target c-Abl, we hypothesized that inhibition of c-Abl underlies the protective effects of imatinib. Surprisingly, neither the inhibition of c-Abl, PDGFR, or c-KIT is responsible for the barrier protective effects of imatinib observed (FIG. 3). siRNA against ARG, however, demonstrated that it is in fact the inhibition of ARG kinase activity which mediates the barrier protective effects of imatinib (FIG. 4). Our data suggest that, whereas Arg mediates endothelial barrier dysfunction, c-Abl supports endothelial barrier function (FIG. 3A and FIG. 7A).

These findings suggest that short term treatment with an ARG inhibitor, e.g., imatinib, would benefit syndromes characterized by endothelial barrier dysfunction.

Accordingly, in one aspect, the disclosure provides a method for the treatment of an individual suffering from or at risk of suffering from inflammatory edema comprising administering an inhibitor of Abl-related gene (ARG) function to said individual thereby treating said edema in said individual.

Edema can be defined as an abnormal accumulation of fluid in the interstices of cells in tissue spaces or in body cavities. It can be caused either by excessive movement of fluid from the vascular system into the tissues or inadequate movement of fluid from the tissues back to the vascular system. The normal interchange of fluid between these two compartments depends on the balance of osmotic pressure and hydrostatic pressure acting in opposite directions across the semi-permeable capillary walls. Edema is the result of an imbalance in these forces, which tends to cause abnormal accumulation of fluid in the interstitial spaces.

Edema may be characterized as inflammatory or non-inflammatory. The composition of the extravascular fluid that accumulates in edema varies according to its etiology. In the case of edema caused by non-inflammatory mechanisms, the fluid (transudate) comprises a relatively low protein concentration and is of less specific gravity, indicating that the endothelium of the affected site is normal. In such cases, the transudate is essentially an ultrafilterate of blood plasma. This kind of non-inflammatory edema is primarily caused by alterations in the hemodynamic forces across the capillary wall and is also known as hemodynamic edema. On the other hand, in the case of edema that is caused by an inflammatory response, the extravascular fluid (exudate) comprises a high concentration of protein, cells and cellular debris and has high specific gravity. This indicates a significant alteration in the normal permeability of the small blood vessels in the affected area.

An increase in vascular permeability is one of the main characteristics of the inflammatory response of the body against stimuli, especially in the case of acute inflammation. In fact, edema is one of the main signs of acute inflammation. During inflammation, the chemical factors derived from plasma and triggered by inflammatory stimuli mediate a number of vascular and cellular responses in the affected site. These structural changes in the microvasculature result in increased permeability of the blood vessel membrane, causing movement of plasma proteins and cells, e.g. leukocytes from the circulation to the intersititium, which ultimately results in site-specific edema. Inflammatory edema can be largely attributed to the direct action of histamine, bradykinin and other the substances released. The main mechanisms of increased vascular permeability in inflammation include endothelial cell contraction, junctional retraction, direct injury, leukocyte-dependent leakage, regenerating endothelium, amongst others. Increased fluid filtration towards the interstitium is further enhanced by the arteriolar vasodilator action of the inflammatory mediators, which increases the blood flow, the perfused surface area, capillary hydrostatic pressure, and facilitates edema by other mechanisms as well. Preferably, the inflammatory edema affects an organ other than the lung and/or the brain.

Preferably, the inflammatory edema treated is thrombin-induced edema, e.g., edema formation after intracerebral hemorrhage. Preferably, the inflammatory edema is histamine induced edema. Preferably, the inflammatory edema is due to endothelial barrier dysfunction. Endothelial barrier dysfunction may be defined functionally, e.g., as an increased passage of macromolecules over a cultured endothelial monolayer or a decreased resistance over an endothelial monolayer, or morphologically, e.g., by the presence of intercellular gaps in an endothelial monolayer.

Preferably, an individual suffering from or at risk of suffering from inflammatory edema is suffering from sepsis, systemic capillary leak syndrome, Acute Lung Injury/Acute Respiratory Distress Syndrome (ALI/ARDS), preeclampsia, no reflow stenosis, pulmonary edema (preferably post-radiation pulmonary edema or post-endarteriectomy pulmonary edema). Sepsis is defined as the presence and growth of micro-organisms in the circulation. One means for diagnosis includes if two or more of the following criteria are present: abnormal body temperature (<36° C. or >38° C.), abnormal white blood cell counts (<4 or >12×109/L), a microbiologically proven or clinical source of infection, tachycardia (>90/min) and tachypnea (>20/min or a partial pressure of arterial carbon dioxide ($P_aCO_2$)<32 mmHg). ALI/ARDS may develop as a consequence of pulmonary diseases (e.g. pneumonia, lung contusion or drowning), or as a consequence of systemic disease (e.g. sepsis). ALI and ARDS are diagnosed according to the American European Consensus Conference criteria. Severe pulmonary edema may follow radiotherapy, depending on the dose and duration of irradiation. Pulmonary edema upon irradiation is diagnosed by evidence for pulmonary edema on chest X-ray or CT of the thorax and hypoxemia. Reperfusion pulmonary edema occurs usually occurs within 72 h after pulmonary endarterectomy (Levinson et al. J Thorac Cardiovasc Surg. 1990 April; 99(4):670-8; Levinson et al. Am Rev Respir Dis. 1986 December; 134(6):1241-5), and is diagnosed by presence of pulmonary edema on chest X-ray or CT (thorax), arterial oxygen tension and hemoglobin oxygen saturation. No reflow stenosis is a phenomen commonly observed during heart catheterization for stenosis of coronary arteries, which is likely caused by edema formation in the vascular wall surrounding the lesion. Preeclampsia refers to a condition in which hypertension arises in association with significant amounts of protein in the urine.

In an additional aspect, a method is provided for inhibiting endothelial barrier dysfunction in a collection of endothelial cells comprising an endothelial barrier that dysfunctions or is at risk of dysfunction, said method comprising providing said collection of endothelial cells with an inhibitor of Abl-related gene (ARG) function. In some embodiments, the collection of endothelial cells are provided with an inhibitor in vitro.

In an additional aspect, a collection of endothelial cells is provided comprising an endothelial barrier that dysfunctions or is at risk of dysfunction, said cells comprising an inhibitor of Abl-related gene (ARG) function.

An inhibitor of Abl-related gene (ARG) function refers to the inhibition or alteration of the ARG gene, ARG mRNA, or ARG protein. An exemplary human ARG protein sequence is MGQQVGRVGEAPGLQQPQPR-GIRGSSAARPSGRRRDPAGRTTETGFNIFTQ HDHFAS-CVEDGFEGDKTGGSSPEALHRPYGCDVE-PQALNEAIRWSSKENL LGATESDPNLFVALYDFVASGDNTLSIT-KGEKLRVLGYNQNGEWSEVRSK NGQGWVPSNYIT-PVNSLEKHSWYHGPVSRSAAEY-LLSSLINGSFLVRESES SPGQLSISLRYEGRVYHYRINT-TADGKVYVTAESRFSTLAELVHHHSTVAD GLVTTL-HYPAPKCNKPTVYGVSPIHDKWEMERT-DITMKHKLGGGQYGEVY VGVWKKYSLTVAVKTLKEDT-MEVEEFLKEAAVMKEIKHPNLVQLLGVCTL EPP-FYIVTEYMPYGNLLDYLRECNREEVTAV-VLLYMATQISSAMEYLEKKN FIHRDLAARNCLVGENHVVKVADFGLSR-LMTGDTYTAHAGAKFPIKWTAP ESLAYNTFSIKSD-VWAFGVLLWEIATYGMSPYPGIDLSQVY-DLLEKGYRME QPEGCPPKVYELMRACWKWSPADRPSFA-ETHQAFETMFHDSSISEEVAEE LGRAASSSSVVPYL-PRLPILPSKTRTLKKQVENKENIEGAQDATENSASSLA PGFIRGAQASSGSPALPRKQRDKSPSS-LLEDAKETCFTRDRKGGFFSSFMK KRNAPTPP-KRSSSFREMENQPHKKYELTGNFSS-VASLQHADGFSFTPAQQ EANLVPPKCYGGSFAQRN-LCNDDGGGGGSGTAGGGWSGITGFFTPRLIK KTLGLRAGKPTASDDTSKPF-PRSNSTSSMSSGLPEQDRMAMTLPRNCQRS KLQ-LERTVSTSSQPEENVDRANDMLPKKSEE-SAAPSRERPKAKLLPRGATA LPLRTPSGDLAITEKDP-PGVGVAGVAAAPKGKEKNGGARLGMAGVPEDGE QPGWPSPAKAAPVLPTTHNHKVPV-LISPTLKHTPADVQLIGTDSQGNKFKL LSEHQVTSS-GDKDRPRRVKPKCAPPPPPVMRLLQHP-SICSDPTEEPTALTA GQSTSETQEGGKKAALGAVPISGKAGR-PVMPPPQVPLPTSSISPAKMANGT AGTKVALRKT-KQAAEKISADKISKEALLECADLLSSAL-TEPVPNSQLVDTG HQLLDYCSGYVDCIPQTRNK-FAFREAVSKLELSLQELQVSSAAAGVPGTNP VLNNLLSCVQEISDVVQR. Inhibitors of ARG function are provided for use in the treatment of an individual suffering from or at risk of suffering from inflammatory edema as described herein.

In a preferred embodiment, the ARG inhibitor preferentially inhibits the non-myristoylated isoform Arg 1a. In a preferred embodiment, the ARG inhibitor preferentially inhibits the non-myristoylated isoform Arg 1b[40].

Preferably, an inhibitor of ARG function inhibits the tyrosine kinase activity of the protein encoded by ARG. Preferable examples of such inhibitors include compounds disclosed in U.S. Pat. Nos. 5,521,184 and 7,169,791 as well as nilotinib or a pharmaceutically acceptable salt thereof (preferably nilotinib hydrochloride monohydrate, i.e., Tasigna™); and dasatinib (Sprycel™) or a pharmaceutically acceptable salt thereof. Nilotinib is chemically described as 4-methyl-N-[3-(4-methyl-1H-imidazol-1-yl)-5-(trifluoromethyl)phenyl]-3-[[-4-(3-pyridinyl)-2-pyrimidinyl]amino]-benzamide and its preparation is described in U.S. Pat. No. 7,169,791. Dasatinib is chemically described as N-(2-chloro-6-methylphenyl)-2-[[6-[4-(2-hydroxyethyl)-1-pipe razinyl]-2-methyl-4-pyrimidinyl]amino]-5-thiazolecarboxamide and its preparation is described in U.S. Pat. No. 6,596,746. In some embodiments, the side effects of dasatinib will be unacceptable and the inhibitor used will not be dasatinib. In some embodiments, the inhibitor is not nilotinib.

More preferred compounds are imatinib or a pharmaceutically acceptable salt thereof mesylate (preferably imatinib mesylate, also referred to as STI-571, CGP 57148 and Gleevec™). Imatinib is chemically described as 4-[(4-methyl-1-piperazinyl)methyl]-N-[4-methyl-3-[[(4-(3-pyridinyl)-2-pyrimidinyl]amino]-phenyl]benzamide methane sulfonate and its preparation is described in U.S. Pat. No. 5,521, 184.

Other small molecule inhibitors that inhibit the tyrosine kinase activity of ARG protein are also suitable. as well as antibodies that bind ARG and inhibit function. The term "antibody" includes, for example, both naturally occurring and non-naturally occurring antibodies, polyclonal and monoclonal antibodies, chimeric antibodies and wholly synthetic antibodies and fragments thereof, such as, for example, the Fab', F(ab')2, Fv or Fab fragments, or other antigen recognizing immunoglobulin fragments. Methods of making antibodies are well known in the art. Preferably, an inhibitor of ARG function inhibits the tyrosine kinase activity of the ARG protein by at least 10%, 20%, 30%, 40%, 50%, 80%, 90% or more as compared to the tyrosine kinase activity of untreated ARG protein.

Preferably, an ARG inhibitor exhibits an IC50 concentration for ARG tyrosince kinase activity of less than 1 micromolar, more preferably the ARG inhibitor has an IC50 concentration of 0.5 micromolar or less. The IC50 of imatinib for ARG tyrosine kinase activity has been reported as 0.5 micromolar (Okuda et al. Blood, 2001).

Preferably, an inhibitor of ARG tyrosine kinase activity specifically inhibits the tyrosine kinase activity of the protein encoded by ARG. Specific inhibition refers to an inhibitor that inhibits ARG tyrosine kinase activity at least two times, preferably at least five times, or at least 10 times greater than it inhibits the tyrosine kinase activity of c-Abl.

Preferably, the specific tyrosine kinase activity inhibitor does not significantly inhibit the tyrosine kinase activity of C-kit, PDGFR-alpha and/or C-Abl.

In some embodiments, the ARG inhibitor is a nucleic acid molecule whose presence in a cell causes the degradation of or inhibits the function, transcription, or translation of its target gene, i.e., ARG, in a sequence-specific manner. Exemplary nucleic acid molecules include aptamers, siRNA, artificial microRNA, interfering RNA or RNAi, dsRNA, ribozymes, antisense oligonucleotides, and DNA expression cassettes encoding said nucleic acid molecules.

Preferably, the nucleic acid molecule is an antisense oligonucleotide. Antisense oligonucleotides (ASO) generally inhibit their target by binding target mRNA and sterically blocking expression by obstructing the ribosome. ASOs can also inhibit their target by binding target mRNA thus forming a DNA-RNA hybrid that can be a substance for RNase H. ASOs may also be produced as composite structures of two or more oligonucleotides, modified oligonucleotides, oligonucleosides, oligonucleotide mimetics, or regions or portions thereof. Such compounds have also been referred to in the art as hybrids or gapmers. Methods for designing and modifying such gapmers are described in, for example, U.S. Patent Publication Nos. 20110092572 and 20100234451.

Recently it has been demonstrated that antisense oligonucleotides can also be used to alter pre-mRNA processing, herein referred to as "exon-skipping" AONs. Antisense oligonucleotides for exon-skipping typically enable skipping of an exon or the 5' or 3' part of it. Antisense oligonucleotides can be directed toward the 5' splice site, the 3' splice, to both splice sites, to one or more exon-internal sites and to intron sequences, for instance specific for the branch point. The latter enables skipping of the upstream exon. An oligonucleotide is said to be directed toward an exon internal sequence if the complementarity region that contains the sequence identity to the reverse complement of the target pre-mRNA is within the exon boundary. Methods for designing exon-skipping oligonucleotides have been described (see, e.g., Aartsma-Rus et al Mol Ther 17(3):548 (2009)).

Preferably, the AONs useful in the methods described herein have a least one chemical modification that increases resistance of the compound to RNase H cleavage. Such modifications include, but are not limited to, nucleotides with sugar modifications. As used herein, a nucleotide with a modified sugar includes, but is not limited to one or more sugar moieties that are mono- or disubstituted at the 2', 3' and/or 5' position such as a —OH; —F; substituted or unsubstituted, linear or branched lower (Cl—ClO) alkyl, alkenyl, alkynyl, alkaryl, allyl, aryl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-0-alkyl, -methoxy, -aminopropoxy; -amino xy; methoxyethoxy; -dimethylaminooxyethoxy; and -dimethylaminoethoxyethoxy. The sugar moiety can be a pyranose or derivative thereof, or a deoxypyranose or derivative thereof, preferably a ribose or a derivative thereof, or a deoxyribose or a derivative thereof. Such preferred derivatized sugar moieties comprise Locked Nucleic Acid (LNA), in which the 2'-carbon atom is linked to the 3' or 4' carbon atom of the sugar ring thereby forming a bicyclic sugar moiety. A preferred LNA comprises 2'-0,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

AONs may also comprise modified backbones, such as morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Preferably, the AON has a phosphorodiamidate morpholino backbone. These oligomers have an uncharged backbone in which the deoxyribose sugar of DNA is replaced by a six membered ring and the phosphodiester linkage is replaced by a phosphorodiamidate linkage. A preferred nucleotide analogue or equivalent comprises a Peptide Nucleic Acid (PNA), having a modified polyamide backbone (Nielsen, et al. (1991) Science 254, 1497-1500).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, an AON comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

It is understood by a skilled person that it is not necessary for all positions in an oligonucleotide to be modified uniformly. In addition, more than one of the aforementioned analogues or equivalents may be incorporated in a single oligonucleotide or even at a single position within an oligonucleotide. In certain embodiments, an oligonucleotide of the invention has at least two different types of analogues or equivalents.

A preferred AON comprises a T-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives. A most preferred AON according to the invention comprises of 2'-O-methyl phosphorothioate ribose.

AONs typically comprise between 12 to 80, preferably between 15 to 40, nucleobases. Preferably, the AONs comprise a stretch of at least 8 nucleobases having 100% complementarity with the target mRNA.

Preferably, the nucleic acid molecule is an RNAi molecule, i.e., RNA interference molecule. Preferred RNAi molecules include siRNA, shRNA, and artificial miRNA.

siRNA comprises a double stranded structure typically containing 15 to 50 base pairs and preferably 19 to 25 base pairs and having a nucleotide sequence identical or nearly identical to an expressed target gene or RNA within the cell. An siRNA may be composed of two annealed polynucleotides or a single polynucleotide that forms a hairpin structure. As used herein "shRNA" or "small hairpin RNA" (also called stem loop) is a type of siRNA. In one embodiment, these shRNAs are composed of a short, e.g. about 10 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The design and production of siRNA molecules is well known to one of skill in the art (Hajeri P B, Singh S K. Drug Discov Today. 2009 14(17-18):851-8). Methods of administration of therapeutic siRNA is also well-known to one of skill in the art (Manjunath N, and Dykxhoorn D M. Discov Med. 2010 May; 9(48):418-30; Guo J et al., Mol Biosyst. 2010 Jul. 15; 6(7):1143-61). siRNA molecule comprises an antisense strand having about 15 to about 30 (e.g., about 15, 16, 17, 18, 19, 20, 21, 22, 23, 24, 25, 26, 27, 28, 29, or 30) nucleotides, wherein the antisense strand is complementary to a RNA sequence or a portion thereof encoding. siRNA against ARG is also commercially available (see, e.g., Invitrogen™ catalog numbers HSS100051, HSS100052, and HSS178493) and described in U.S. Patent Publication No. 20050246794.

Artificial miRNA molecules are pre-miRNA or pri-miRNA comprising a stem-loop structure(s) derived from a specific endogenous miRNA in which the stem(s) of the stem-loop structure(s) incorporates a mature strand-star strand duplex where the mature strand sequence is distinct from the endogenous mature strand sequence of the specific referenced endogenous miRNA. The sequence of the star strand of a non-naturally occurring miRNA of the disclosure is also distinct from the endogenous star strand sequence of the specific referenced endogenous miRNA. Many microRNA precursors can be used, including without limitation a microRNA comprising a backbone design of miR-15a, -16, -19b, -20, -23a, -27b, -29a, -30b, -30c, -104, -132s, -181, -191, -223 (See, e.g., U.S. Patent Publication Nos. 20050075492 and 20100292310 for the design and production of artificial miRNA molecules).

RNA interference refers to a decrease in the mRNA level in a cell for a heterologous target gene by at least about 5%, about 10%, about 20%, about 30%, about 40%, about 50%, about 60%, about 70%, about 80%, about 90%, about 95%, about 99%, about 100% of the mRNA level found in the cell without the presence of the, e.g., miRNA or siRNA interference molecule RNAi molecules may also include chemical analogues such as, e.g., 2'-O-Methyl ribose analogues of RNA, DNA, LNA and RNA chimeric oligonucleotides, and other chemical analogues of nucleic acid oligonucleotides.

The nucleic acid molecule inhibitors may be chemically synthesized and provided directly to cells of interest. The nucleic acid compound may be provided to a cell as part of a gene delivery vehicle. Such a vehicle is preferably a liposome or a viral gene delivery vehicle. Liposomes are well known in the art and many variants are available for gene transfer purposes. Various viral gene delivery are currently used to transfer genes into target cells. In the present disclosure it is preferred to use those viral vectors that do not express their own genes but only the transferred genes. The nucleic acid compound may be present as such in the gene delivery vehicle. In a viral vector, the nucleic acid compound is preferably provided as an expression cassette wherein the expression cassette encodes a transcript comprising said compound.

Accordingly, the nucleic acid molecule inhibitors may be provided in. A "vector" is a recombinant nucleic acid construct, such as plasmid, phase genome, virus genome, cosmid, or artificial chromosome, to which another DNA segment may be attached. The term "vector" includes both viral and nonviral means for introducing the nucleic acid into a cell in vitro, ex vivo or in vivo. Non-viral vectors include plasmids, liposomes, electrically charged lipids (cytofectins), DNA-protein complexes, and biopolymers. Viral vectors include retrovirus, adeno-associated virus, pox, baculovirus, vaccinia, herpes simplex, Epstein-Barr and adenovirus vectors, as set forth in greater detail below. Vector sequences may also contain one or more regulatory regions, and/or selectable markers useful in selecting, measuring, and monitoring nucleic acid transfer results (transfer to which tissues, duration of expression, etc.).

Preferably, the vector sequences provide delivery of the nucleic acid molecules to the appropriate cells. A preferred delivery vehicle is a viral vector such as an adeno-associated virus vector (AAV), or a retroviral vector such as a lentivirus vector and the like (Goyenvalle A, et al. Science 2004; 306 (5702):1796-9).

Also plasmids, artificial chromosomes, plasmids suitable for targeted homologous recombination and integration in the human genome of cells may be suitably applied for delivery of a nucleic acid compound. Preferred are those vectors wherein transcription is driven from Pol III promoters, and/or wherein transcripts are in the form fusions with U1 or U7 transcripts, which yield good results for delivering small transcripts. It is within the skill of the artisan to design suitable transcripts. Preferred are Pol III driven transcripts.

In contrast to studies reporting subcutaneous edema as a consequence of long term imatinib treatment, the present disclosure demonstrates that short-term treatment with imatinib protects against endothelial barrier dysfunction. Accordingly, it is preferred in the methods described herein that the inhibitor of ARG function is provided to an individual for a time period of between 1-20 weeks. Preferably, the inhibitor is provided for a time period of between 1-12 weeks, more preferably the inhibitor is provided for up to 3 weeks.

The inhibitor of ARG function may be formulated into any suitable pharmaceutical preparation for administration and further comprising, e.g., a pharmaceutically acceptable carrier, filler, preservative, adjuvant, solubilizer, diluent and/or excipient. Such pharmaceutically acceptable carrier, filler, preservative, adjuvant, solubilizer, diluent and/or excipient may for instance be found in Remington: The Science and Practice of Pharmacy, 20th Edition. Baltimore, Md.: Lippincott Williams & Wilkins, 2000. If the inhibitor is a nucleic acid compound, the preferred excipients are capable of forming complexes, vesicles and/or liposomes that deliver such a through a cell membrane. Suitable excipients include polyethylenimine (PEI) or similar cationic polymers, including polypropyleneimine or polyethylenimine copolymers (PECs) and derivatives, ExGen 500, synthetic amphiphils (SAINT-18), Lipofectin™, and DOTAP.

A skilled person can determine the administration route for such pharmaceutical preparations, such as by oral, intravenous, subcutaneous, intramuscular, intrathecal and/or intraventricular administration. Preferably the inhibitor is administered orally or intravenously.

A skilled person can readily determine a suitable dose and dosage regiment of inhibitor for administration. An exemplary dose of imatinib, for example, is a daily dose of 400 mg resulting in imatinib plasma levels between 1 and 10 micromolar (Singh et al, Eur J Clin Pharmacol (2009) 65:545-549). If clinical response is not observed within a few days from onset of treatment the dosage can be increased, for example to 400 mg twice daily.

BRIEF DESCRIPTION OF THE DRAWINGS

FIG. 1—Imatinib attenuates thrombin-induced endothelial barrier dysfunction through stabilization of adherens junctions. To test the effects of imatinib on endothelial barrier, HUVECs were seeded on polycarbonate filters (HRP passage) or ECIS gold electrodes (resistance measurements) and grown to confluence. Confluent cells were pretreated with imatinib or DMSO (0.1%), and stimulated with thrombin (IIa, 1 U/mL) or vector. A) Time curve of HRP passage in the presence or absence of imatinib. Mean±SEM of N=4 experiments, each representing triplo measurements. $P<0.01$, *$P<0.001$ compared to DMSO+IIa. B) Effects of imatinib on normalized endothelial resistance during thrombin stimulation. Absolute resistance was normalized to the moment just before addition of thrombin. Mean±SEM of N=5 experiments, each representing duplo measurements. C) Quantification of the maximum decrease in normalized resistance as measured in B. Mean±SEM of N=4 experiments, each representing duplo measurements. ***$P<0.001$. D) HRP passage over human pulmonary microvascular endothelial cell (HPMVEC) monolayers grown on polycarbonate filters (HRP passage). Cells were pretreated with imatinib (10 µM) or (DMSO 0.1%), and subsequently stimulated with thrombin (IIa, 1 U/mL) or vector. Mean±SEM of 5-6 measurements in N=2 experiments. E) HUVECs were grown to confluence on glass coverslips, pretreated with DMSO (upper panels) or imatinib 10 µM (lower panels) and stimulated with thrombin for 30 min. Fixated cells were stained for VE-cadherin (green) and the nucleus (DAPI, blue). Representative images of N=3 experiments. F) Immunofluorescence staining of β-catenin after 30 min of thrombin stimulation. Representative images of N=2 experiments. Scale bars represent 20 µm. All arrows indicate loss of staining at the membrane, suggesting intercellular gaps. Imaging was performed with a Axiovert 200 Marianas inverted wide-field fluorescence microscope, using a 40× Zeiss air lens (NA 0.75).

FIG. 3—Inhibition of c-Abl, PDGFR or c-KIT does not underlie the protective effects of imatinib. HUVECs were transfected with siRNA against c-Abl, PDGFR-α and -β, c-KIT or scrambled RNA (scRNA), using Amaxa Technology. After transfection, cells were seeded on 5 cm² wells for Western Blot analysis or on ECIS gold electrodes, and grown to confluence for 48 h. Cells were pretreated with 1% HSA/M199, and subsequently stimulated with thrombin (IIa, 1 U/mL). A) siRNA treatment resulted in an 80-90% decrease in c-Abl protein expression, as confirmed by Western Blot analysis for total c-Abl. β-actin served as loading control (insert). Absolute resistance under control or thrombin stimulated conditions. Mean±SEM of 4 measurements in N=2 experiments. B) Thrombin-induced decrease in normalized endothelial resistance after transfection with c-Abl siRNA or scRNA. Resistance was normalized to the moment just before addition of thrombin. Mean±SEM of N=4 measurements in 2 independent experiments. C) Thrombin-induced decrease in normalized endothelial resistance after knock down of PDGFR-α, -β or the combination. Resistance was normalized to the moment just before addition of thrombin. Mean±SEM of 4 measurements in N=2 experiments. D) The effect of c-KIT knock down on thrombin-induced drop in normalized endothelial resistance. Resistance was normalized to the moment just before addition of thrombin. Mean±SEM of N=3 experiments, each representing duplo measurements.

FIG. 5

Figure 2B:
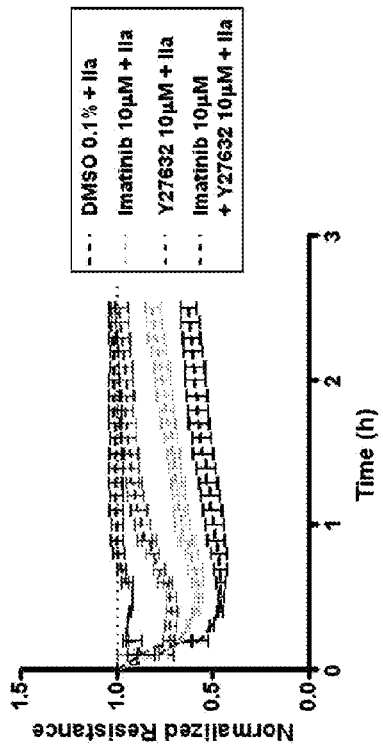
FIG. 2—Imatinib inhibits endothelial barrier dysfunction without affecting RhoA/Rho kinase (ROCK) signaling. HUVECs were seeded on polycarbonate filters, ECIS gold electrodes, or glass cover slips and grown to confluence. Confluent cells were pretreated with imatinib (10 µM), the ROCK inhibitor Y-27632 (10 µM) or DMSO (0.1%), and subsequently stimulated with thrombin (IIa, 1 U/mL) or vector. A) F-actin staining (rhodamine/phalloidine) of confluent cells pretreated with imatinib or DMSO and stimulated with thrombin or vector. Scale bars represent 10 µm. Imaging was performed with a Axiovert 200 Marianas inverted wide-field fluorescence microscope, using a 63× Zeiss oil lens (NA 1.4). Representative images of N=2 experiments. B) The effects of imatinib and/or Y-27632 pre-treatment on thrombin-induced HRP passage over HUVEC monolayers after 30 min. Mean±SEM of 6 measurements in N=2 experiments. C) Electrical resistance of HUVEC monolayers during thrombin stimulation, after pretreatment with imatinib, Y-27632 or DMSO. Resistance was normalized to the moment just before addition of thrombin. Mean±SEM of N=3 experiments, each representing duplo measurements. D) Quantification of the maximum decrease in relative resistance as measured in C. Mean±SEM of N=3 experiments. E) Effects of imatinib on thrombin-induced RhoA activation in HUVEC, expressed in arbitrary units (A.U.). Mean±SEM of 4 measurements in N=2 experiments. *$P<0.05$, ***$P<0.001$.
Figure 2D:
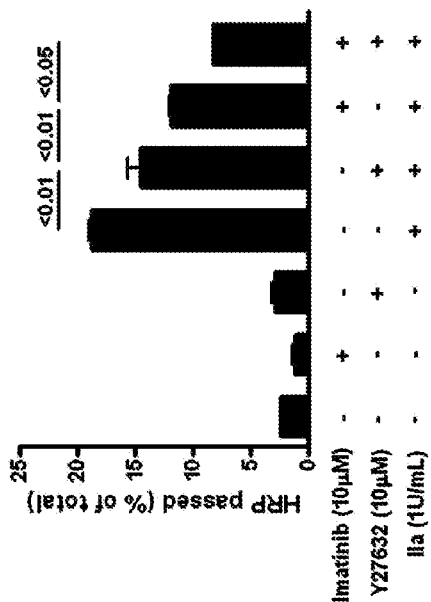

A) HUVECs were seeded on polycarbonate filters and grown to confluence for 120 h. Confluent cells were pretreated with increasing concentrations of imatinib (1, 2, 5, 10 µM) or DMSO (in corresponding concentrations), and stimulated with thrombin (IIa, 1 U/mL) or vector. Mean of N=2 experiments, each representing triplo measurements. B) HPMVECs were seeded on ECIS gold electrodes and grown to confluence. Absolute endothelial resistance of HPMVEC monolayers pretreated with imatinib (10 µM) or DMSO (0.1%), and subsequently stimulated with thrombin (IIa, 1 U/mL). Mean±standard deviation (SD) of 3 measurements in 1 experiment. C) HFMVECs were seeded on ECIS gold electrodes and grown to confluence. Absolute endothelial resistance of human skin microvascular endothelial cell (HSMVEC) monolayers pretreated with imatinib (10 µM) or DMSO (0.1%) and subsequently stimulated with thrombin (IIa, 1 U/mL). Mean±SD of N=3 experiments, each representing duplo measurements.

FIG. 6

HUVECs or HPMVECs were seeded on ECIS gold electrodes. A) Resistance of cell-cell interaction (Rb) in HUVECs during thrombin stimulation (IIa, 1 U/mL) after pretreatment with DMSO (0.1%) or imatinib (10 µM). Mean±SEM of N=3 experiments, each representing duplo measurements. B) Resistance of cell-matrix interaction (Alpha) in HUVECs during thrombin stimulation after pretreatment with DMSO or imatinib. Mean±SEM of N=3 experiments, each representing duplo measurements. C) Resistance caused by cell-cell interaction (Rb) in HPMVECs pretreated with DMSO (0.1%) or imatinib (10 µM), and stimulated with thrombin (IIa, 1 U/mL). D) Resistance caused by cell-matrix interaction (Alpha) in HPMVECs pretreated with DMSO or imatinib, and stimulated with thrombin.

FIG. 7

A) HUVECs were transfected with scRNA or c-Abl siRNA and seeded on ECIS gold electrodes. Cells were grown to confluence for 48 h, pretreated with 1% HSA and stimulated with thrombin (IIa, 1 U/mL). From ECIS measurements the resistance caused by cell-cell interaction (Rb) and the resistance caused by cell-matrix interaction (alpha) were calculated. The effect of c-Abl knock down on the thrombin-induced decrease in normalized Rb is represented here. Mean±SEM of 4 measurements in N=2 experiments. B) Cells were transfected with scRNA or c-Abl siRNA and grown to confluence. After 48 h cells were pretreated with imatinib (10 µM) and subsequently stimulated with thrombin (IIa, 1 U/mL). Mean of N=2 experiments, each representing duplo measurements. C) HUVECs were transfected with scRNA, PDGFR-α or -β siRNA or the combination of PDGFR-α and -β siRNA, seeded on ECIS gold electrodes, and grown to confluence. After 48 h cells were pretreated with 1% HSA, and stimulated with thrombin (IIa, 1 U/mL). Data represent absolute endothelial resistance. D) Time curve of HRP passage in cells transfected with scRNA, PDGFR-α or -β siRNA or a combination of PDGFR-α and -β siRNA after stimulation with thrombin or vector. Mean±SEM of 3-6 measurements in N=2 experiments. E) HUVECs were seeded in 5 cm2 culture wells and grown to confluence. Confluent cells were serum starved for 24 h with medium containing 1% (1% s) or 2% (2% s) new-born calf serum, or cultured under normal growth medium (cM199). After 24 h cells were lysated and cell lysates were analysed for expression of PDGFR-α or -β by Western Blot. Lysates of human lung fibroblasts (FB) served as positive control for PDGFR expression. Representative images of N=3 experiments. F) Quantification of the maximal decrease in normalized resistance in HUVECs pretreated with increasing concentrations of Tyrphostin AG1296 (2, 10, 50 µM) or DMSO (0.1%) and stimulated with thrombin (IIa, 1 U/mL) or vector. Mean±SEM of N=5 experiments, ***P<0.001 compared to DMSO+IIa.

REFERENCE LIST

1. Lee WL, Slutsky AS. Sepsis and endothelial permeability. *N Engl J Med.* 2010; 363(7):689-691.
2. Mehta D, Malik AB. Signaling mechanisms regulating endothelial permeability. *Physiol Rev.* 2006; 86(1):279-367.
3. Overbeek MJ, van Nieuw Amerongen GP, Boonstra A, Smit EF, Vonk-Noordegraaf A. Possible role of imatinib in clinical pulmonary veno-occlusive disease. *Eur Respir J.* 2008; 32(1):232-235.
4. Waller C F. Imatinib mesylate. *Recent Results Cancer Res.* 2010; 184:3-20.
5. Schiffer C A. BCR-ABL tyrosine kinase inhibitors for chronic myelogenous leukemia. *N Engl J Med.* 2007; 357 (3):258-265.
6. Deininger MW, Goldman JM, Lydon N, Melo JV. The tyrosine kinase inhibitor CGP57148B selectively inhibits the growth of BCR-ABL-positive cells. *Blood.* 1997; 90(9):3691-3698.
7. Druker BJ, Talpaz M, Resta DJ et al. Efficacy and safety of a specific inhibitor of the BCR-ABL tyrosine kinase in chronic myeloid leukemia. *N Engl J Med.* 2001; 344(14): 1031-1037.
8. van Oosterom AT, Judson I, Verweij J et al. Safety and efficacy of imatinib (STI571) in metastatic gastrointestinal stromal tumours: a phase I study. *Lancet.* 2001; 358(9291): 1421-1423.

9. Daniels CE, Wilkes MC, Edens M et al. Imatinib mesylate inhibits the profibrogenic activity of TGF-beta and prevents bleomycin-mediated lung fibrosis. *J Clin Invest*. 2004; 114(9):1308-1316.
10. Schermuly RT, Dony E, Ghofrani HA et al. Reversal of experimental pulmonary hypertension by PDGF inhibition. *J Clin Invest*. 2005; 115(10):2811-2821.
11. Kerkela R, Grazette L, Yacobi R et al. Cardiotoxicity of the cancer therapeutic agent imatinib mesylate. *Nat Med*. 2006; 12(8):908-916.
12. Hellberg C, Ostman A, Heldin CH. PDGF and vessel maturation. *Recent Results Cancer Res*. 2010; 180:103-114.
13. Su EJ, Fredriksson L, Geyer M et al. Activation of PDGF-CC by tissue plasminogen activator impairs blood-brain barrier integrity during ischemic stroke. *Nat Med*. 2008; 14(7):731-737.
14. Armulik A, Genove G, Mae M et al. Pericytes regulate the blood-brain barrier. *Nature*. 2010; 468(7323):557-561.
15. van Nieuw Amerongen GP, Draijer R, Vermeer MA, van Hinsbergh VWM. Transient and prolonged increase in endothelial permeability induced by histamine and thrombin: role of protein kinases, calcium, and RhoA. *Circ Res*. 1998; 83(11):1115-1123.
16. Shelton JL, Wang L, Cepinskas G et al. Albumin leak across human pulmonary microvascular vs. umbilical vein endothelial cells under septic conditions. *Microvasc Res*. 2006; 71(1):40-47.
17. van Hinsbergh VWM, Spengers ED, Kooistra T. Effect of thrombin on the production of plasminogen activators and PA inhibitor-1 by human foreskin microvascular endothelial cells. *Thromb Haemost*. 1987; 57(2):148-153.
18. Vogel SM, Gao X, Mehta D et al. Abrogation of thrombin-induced increase in pulmonary microvascular permeability in PAR-1 knockout mice. *Physiol Genomics*. 2000; 4(2): 137-145.
19. Tauseef M, Kini V, Knezevic N et al. Activation of sphingosine kinase-1 reverses the increase in lung vascular permeability through sphingosine-1-phosphate receptor signaling in endothelial cells. *Circ Res*. 2008; 103(10): 1164-1172.
20. Minami T, Sugiyama A, Wu SQ et al. Thrombin and phenotypic modulation of the endothelium. *Arterioscler Thromb Vasc Biol*. 2004; 24(1):41-53.
21. Giaever I, Keese CR. Micromotion of mammalian cells measured electrically. *Proc Natl Acad Sci USA*. 1991; 88(17):7896-7900.
22. Lo CM, Keese CR, Giaever I. Cell-substrate contact: another factor may influence transepithelial electrical resistance of cell layers cultured on permeable filters. *Exp Cell Res*. 1999; 250(2):576-580.
23. Dejana E, Orsenigo F, Lampugnani MG. The role of adherens junctions and VE-cadherin in the control of vascular permeability. *J Cell Sci*. 2008; 121(Pt 13):2115-2122.
24. van Nieuw Amerongen G P, van Delft S, Vermeer MA, Collard JG, van Hinsbergh VWM. Activation of RhoA by thrombin in endothelial hyperpermeability: role of Rho kinase and protein tyrosine kinases. *Circ Res*. 2000; 87(4): 335-340.
25. Huang X, Wu D, Jin H, Stupack D, Wang JYJ. Induction of cell retraction by the combined actions of Abl-CrkII and Rho-ROCK1 signaling. *J Cell Biol*. 2008; 183(4):711-723.
26. Kim J, Wu Q, Zhang Y et al. PDGF signaling is required for epicardial function and blood vessel formation in regenerating zebrafish hearts. *Proc Natl Acad Sci USA*. 2010; 107(40):17206-17210.
27. Hernandez SE, Settleman J, Koleske AJ. Adhesion-dependent regulation of p190RhoGAP in the developing brain by the Abl-related gene tyrosine kinase. *Curr Biol*. 2004; 14(8):691-696.
28. Bradley WD, Hernandez SE, Settleman J, Koleske AJ. Integrin signaling through Arg activates p190RhoGAP by promoting its binding to p120RasGAP and recruitment to the membrane. *Mol Biol Cell*. 2006; 17(11):4827-4836.
29. Kurimoto N, Nan YS, Chen ZY et al. Effects of specific signal transduction inhibitors on increased permeability across rat endothelial monolayers induced by neuropeptide Y or VEGF. *Am J Physiol Heart Circ Physiol*. 2004; 287 (1):H100-H106.
30. Singh N, Kumar L, Meena R, Velpandian T. Drug monitoring of imatinib levels in patients undergoing therapy for chronic myeloid leukaemia: comparing plasma levels of responders and non-responders. *Eur J Clin Pharmacol*. 2009; 65(6):545-549.
31. Demetri GD, Wang Y, Wehrle E et al. Imatinib plasma levels are correlated with clinical benefit in patients with unresectable/metastatic gastrointestinal stromal tumors. *J Clin Oncol*. 2009; 27(19):3141-3147.
32. Wang Y, Miller AL, Mooseker MS, Koleske AJ. The Abl-related gene (Arg) nonreceptor tyrosine kinase uses two F-actin-binding domains to bundle F-actin. *Proc Natl Acad Sci USA*. 2001; 98(26):14865-14870.
33. Galkin VE, Orlova A, Koleske AJ, Egelman E H. The Arg non-receptor tyrosine kinase modifies F-actin structure. *J Mol Biol*. 2005; 346(2):565-575.
34. Lapetina S, Mader CC, Machida K, Mayer BJ, Koleske AJ. Arg interacts with cortactin to promote adhesion-dependent cell edge protrusion. *J Cell Biol*. 2009; 185(3): 503-519.
35. Miller MM, Lapetina S, MacGrath SM et al. Regulation of actin polymerization and adhesion-dependent cell edge protrusion by the Abl-related gene (Arg) tyrosine kinase and N-WASp. *Biochemistry*. 2010; 49(10):2227-2234.
36. Boyle SN, Koleske AJ. Use of a chemical genetic technique to identify myosin IIb as a substrate of the Abl-related gene (Arg) tyrosine kinase. *Biochemistry*. 2007; 46(41):11614-11620.
37. Kolega J. Asymmetric distribution of myosin IIB in migrating endothelial cells is regulated by a rho-dependent kinase and contributes to tail retraction. *Mol Biol Cell*. 2003; 14(12):4745-4757.
38. Peacock JG, Couch BA, Koleske AJ. The Abl and Arg non-receptor tyrosine kinases regulate different zones of stress fiber, focal adhesion, and contractile network localization in spreading fibroblasts. *Cytoskeleton (Hoboken)*. 2010; 67(10):666-675.
39. Shikata Y, Birukov KG, Garcia JGN. SW induces FA remodeling in human pulmonary endothelial cells: role of Rac, GIT1, FAK, and paxillin. *J Appl Physiol*. 2003; 94(3): 1193-1203.
40. Bradley WD, Koleske AJ. Regulation of cell migration and morphogenesis by Abl-family kinases: emerging mechanisms and physiological contexts. *J Cell Sci*. 2009; 122 (Pt 19):3441-3454.
41. Zandy NL, Playford M, Pendergast AM. Abl tyrosine kinases regulate cell-cell adhesion through Rho GTPases. *Proc Natl Acad Sci USA*. 2007; 104 (45):17686-17691.
42. Wang B, Kruh GD. Subcellular localization of the Arg protein tyrosine kinase. *Oncogene*. 1996; 13(1):193-197.
43. Dudek S M, Chiang ET, Camp SM et al. Abl tyrosine kinase phosphorylates nonmuscle Myosin light chain kinase to regulate endothelial barrier function. *Mol Biol Cell*. 2010; 21(22):4042-4056.

The invention is further explained in the following examples. These examples do not limit the scope of the invention, but merely serve to clarify the invention.

EXAMPLES

Example 1

Imatinib Attenuates Thrombin-Induced Endothelial Hyperpermeability

To evaluate the effects of imatinib on endothelial barrier function, HUVECs were pretreated with imatinib, and subsequently stimulated with thrombin (1 U/mL). Thrombin was used to mimick inflammatory conditions, as thrombin is a potent inducer of endothelial permeability,[18,19] and is increased in sepsis and at sites of vascular injury.[20] Endothelial barrier function was evaluated both by the passage of HRP across endothelial monolayers grown on porous filters and by electrical resistance of endothelial monolayers grown on gold electrodes (Electrical Cell-substrate Impedance Sensing [ECIS]). Imatinib did not affect basal endothelial barrier function in both measurements (FIGS. 1A & C). Thrombin induced a 5- to 10-fold increase in HRP passage across endothelial monolayers (FIG. 1A), which was attenuated dose-dependently by imatinib with a maximal effect at 10 μM (FIG. 5A). Imatinib 10 μM reduced the thrombin-induced HRP passage similarly at all time points (35-44% inhibition, P<0.001; FIG. 1A). In ECIS measurements thrombin strongly reduced endothelial electrical resistance reaching a maximum after 30 min, followed by a gradual recovery of EC resistance (FIG. 1B). Imatinib attenuated the thrombin-induced decrease in endothelial resistance, as indicated by a significantly smaller drop in resistance, and a faster recovery towards baseline (FIGS. 1B and 1C, maximal decrease in normalized resistance of −0.54±0.02 in DMSO pretreated vs. −0.41±0.03 in imatinib pretreated cells, P<0.001). To evaluate whether the observed effects of imatinib also occur in other types of endothelial cells, permeability assays were performed in human pulmonary microvascular endothelial cells (HPMVECs) and human foreskin microvascular endothelial cells (HFMVECs). In HPMVECs, imatinib reduced the thrombin-induced macromolecule passage (FIG. 1D) and attenuated the maximal drop in endothelial resistance (FIG. 5B). In a similar fashion, imatinib attenuated the thrombin-induced maximal drop in endothelial resistance in HFMVECs (FIG. 5C).

Example 2

Imatinib Attenuates Thrombin-Induced Disintegration of Endothelial Junctions

Figure 6A:
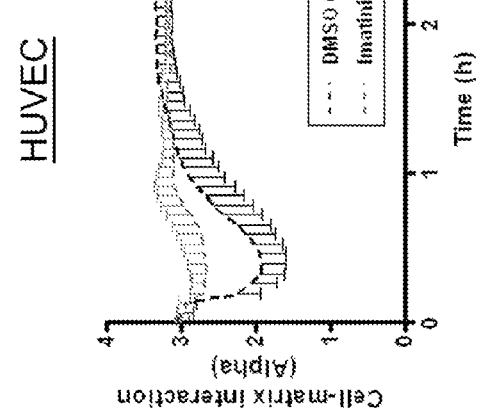
Figure 6B:
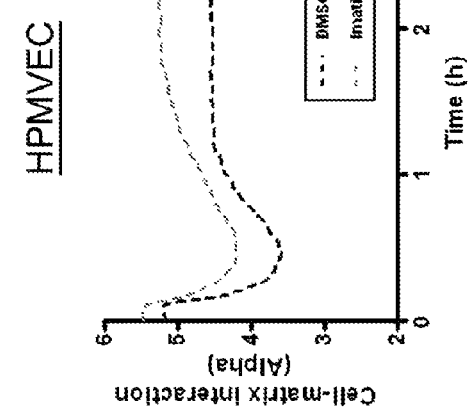
Figure 6C:
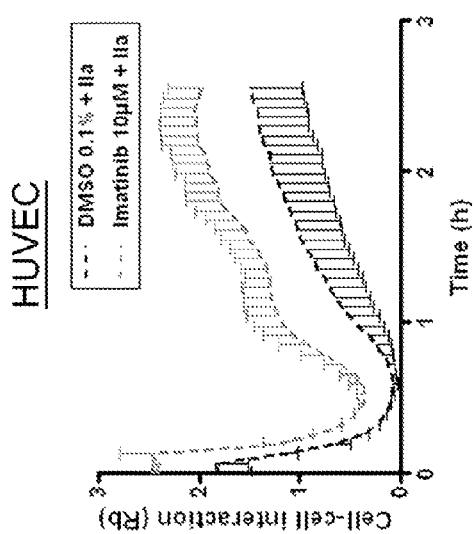
Figure 6D:
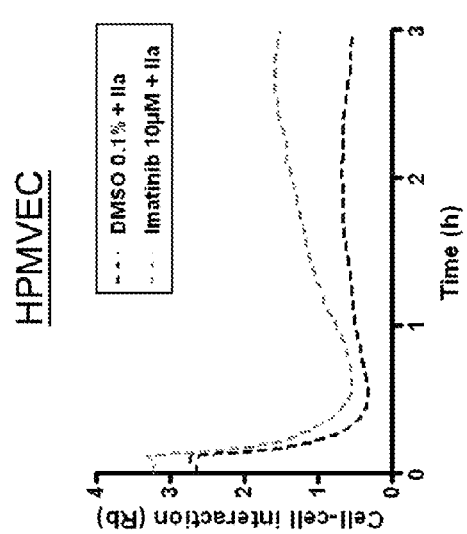

Electrical resistance over an endothelial monolayer results from both cell-cell interaction (intercellular adhesion) and cell-substrate interaction (cell adhesion to subcellular matrix).[21,22] Calculation of the resistance caused by cell-cell interaction (Rb) revealed that thrombin strongly decreases cell-cell adhesion, which was attenuated by imatinib (FIG. 6A, maximal decrease in normalized Rb −0.97±0.02 in DMSO pretreated vs. −0.87±0.03 in imatinib pretreated cells, P=0.05). This was accompanied by attenuation of the thrombin-induced drop in cell-matrix interaction (FIG. 6B). Comparable effects of imatinib on Rb and alpha were observed in HPMVECs (FIGS. 6C & D). To further analyse the effect of imatinib on cell-cell adhesion, we performed immunofluorescence staining of the AJ proteins VE-cadherin and β-catenin, both of which are required for AJ integrity.[2,23] At 15 min (data not shown) and 30 min, thrombin induced loss of VE-cadherin (FIG. 1E) and β-catenin (FIG. 1F) from the membrane, as indicated by a reduction of fluorescence signal at the cell periphery, and formation of intercellular gaps (arrows, FIGS. 1E & F). The loss of VE-cadherin and β-catenin from the membrane could be partly reversed by pretreatment with imatinib, indicated by preservation of membrane staining and reduction of the number of intercellular gaps.

Altogether, these data demonstrate that imatinib protects against endothelial barrier dysfunction during thrombin stimulation. Imatinib exerts these effects by preservation of AJ integrity and cell-cell adhesion.

Example 3

The Barrier Protective Effects of Imatinib are Independent from the RhoA/Rho Kinase Pathway Thrombin-induced AJ dissociation and loss of cell-cell adhesion involves $Ca^{2+}$ and RhoA/Rho kinase mediated actin-myosin contraction.[2,24] To evaluate actin-myosin contraction, HUVECs were stained for F-actin. Thrombin (15 min) altered the F-actin cytoskeleton from a predominant peripheral F-actin band (FIG. 2A, upper left panel) into a new pattern with robust F-actin stress fibers (arrows, FIG. 2A, upper right panel). In imatinib pretreated cells F-actin was not organized in F-actin stress fibers, but in a fine-structured network of small F-actin filaments at the cell periphery. The absence of stress fibers in imatinib pretreated cells was associated with loss of contractile cell morphology and less intercellular gaps (FIG. 2A, lower right panel).

Figure 2C:
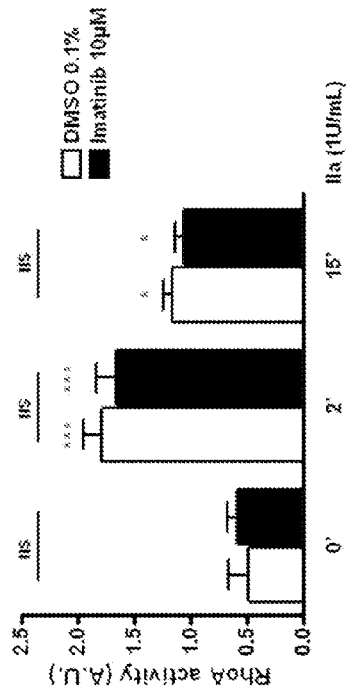

Since most imatinib-sensitive kinases (c-Abl[25], PDGFR[26] and Arg[27,28]) have been reported to affect Rho kinase activity, we hypothesized that imatinib attenuates the thrombin-induced changes in actin cytoskeleton via inhibition of the RhoA/Rho kinase pathway. HUVECs were pretreated with imatinib and/or the Rho kinase inhibitor Y-27632, and stimulated with thrombin. Both imatinib and Y-27632 reduced the thrombin-induced endothelial permeability as determined by HRP passage and transendothelial electrical resistance. The inhibitory effects of imatinib and Y-27632 on HRP passage were independent and additive (FIG. 2B, P<0.05). Similarly, the ECIS measurements pointed to an additive effect of imatinib and Y-27632 (FIGS. 2C and D, maximal drop in electrical resistance of −0.44±0.02 in cells pretreated with imatinib alone vs. −0.18±0.04 in cells pretreated with a combination of imatinib and Y-27632, P<0.05).

Figure 2E:
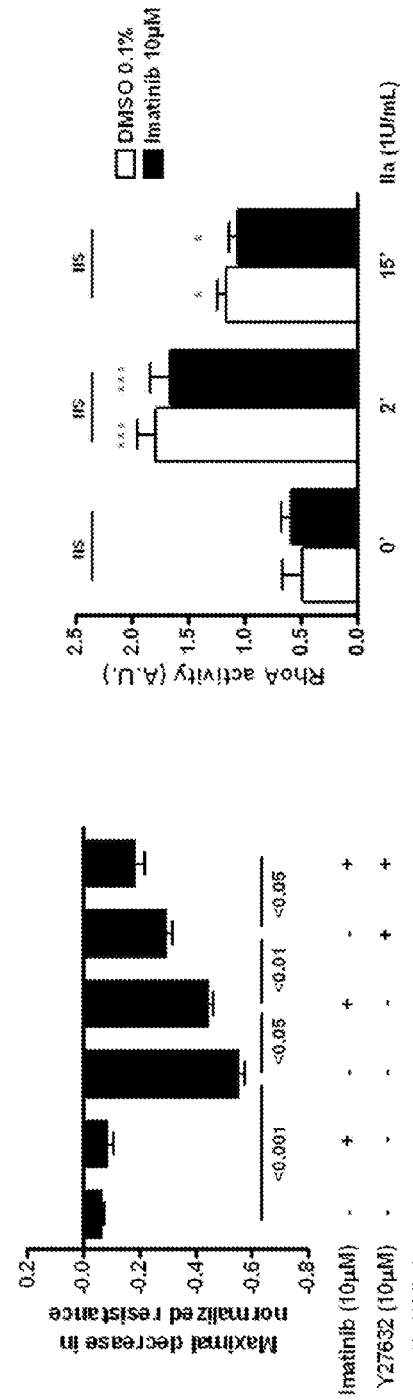

To analyse the effect of imatinib on RhoA activation, cell lysates were analysed for RhoA activity with a G-LISA RhoA Activity Assay. RhoA activity strongly increased upon thrombin stimulation, but was not affected by pretreatment with imatinib (FIG. 2E). Since imatinib does not affect RhoA activation and has an additive effect to ROCK inhibition, imatinib attenuates endothelial permeability independent of the RhoA/Rho kinase pathway. Using BAPTA-AM as a chelator of intracellular calcium, an effect of imatinib on cytoplasmic $Ca^{2+}$ was also excluded (data not shown).

These data indicate that imatinib reduces F-actin stress fiber formation and cell contraction without affecting the RhoA/Rho kinase pathway. It implicates that, during endothelial barrier dysfunction, there is regulation of F-actin structure independent of the RhoA/Rho kinase pathway.

Example 4

Figure 7A:
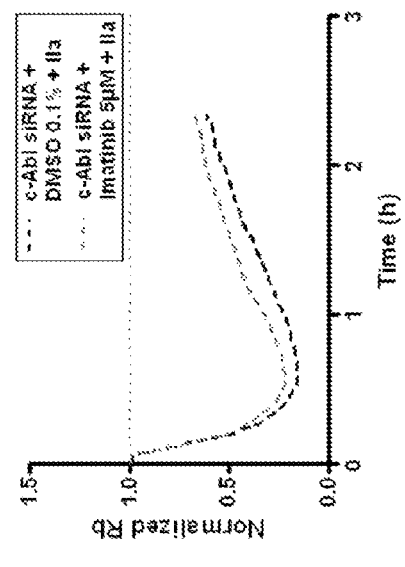
Figure 7B:
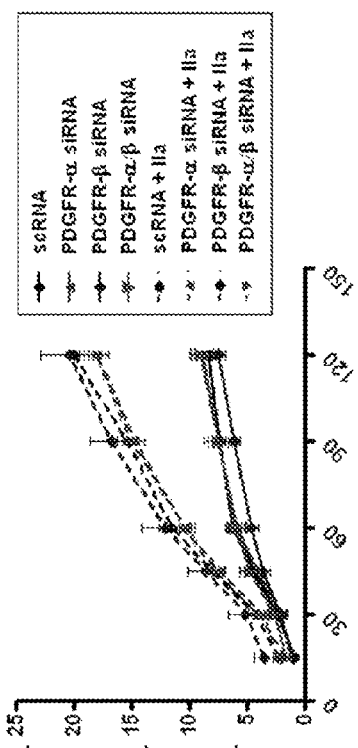

Inhibition of c-Abl, PDGFR or c-Kit does not Underlie the Barrier Protective Effects of Imatinib To determine which of the imatinib-sensitive kinases (c-Abl, PDGFR, Arg and c-KIT) is involved in thrombin-induced endothelial hyperpermeability, a systematic siRNA knock down of the imatinib sensitive kinases was performed. As imatinib was primarily developed to target c-Abl, we hypothesized that inhibition of c-Abl underlies the protective effects of imatinib. HUVECs were transfected with c-Abl siRNA to knock down c-Abl, resulting in an 85% reduction in c-Abl protein expression compared to transfection with scrambled RNA (scRNA, FIG. 3A insert). ECIS measurements demonstrated that c-Abl knock down somewhat impaired basal endothelial barrier integrity (reduction of 100Ω compared to control cells, FIG. 3A). Thrombin induced an identical decrease in electrical resistance in control and c-Abl deficient cells (FIGS. 3A and 3B). However, calculation of Rb revealed that the thrombin-response was more prominent in c-Abl deficient endothelial cells (FIG. 7A). In c-Abl deficient cells, imatinib still attenuated the thrombin response (FIG. 7B). Thus, inhibition of c-Abl does not underlie the protective effects of imatinib on endothelial barrier function.

Figure 7C:
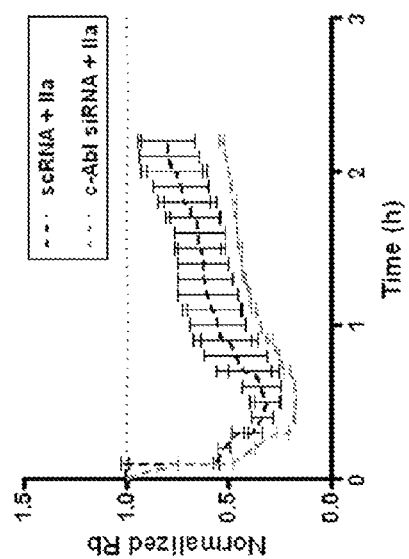
Figure 7D:
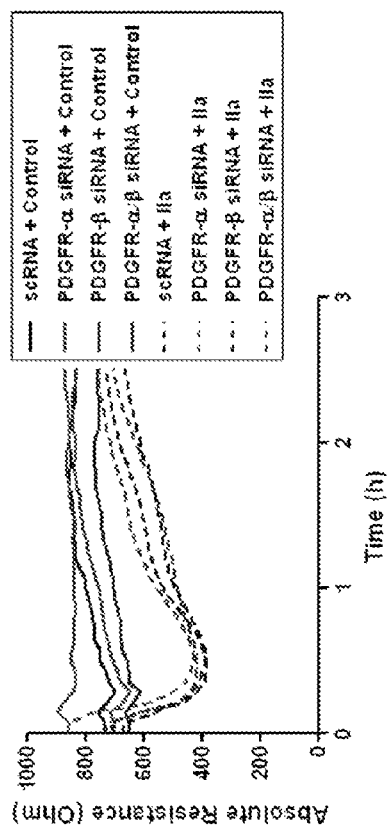

Subsequently, we tested whether inhibition of PDGFR was responsible for the effects of imatinib on endothelial permeability. HUVECs were transfected with siRNA against PDGFR-α or -β, or the combination. Although combined knock down of PDGFR-α and -β increased basal endothelial resistance (FIG. 7C), no protective effect on the thrombin response was observed (FIG. 3C). Similarly, no difference in HRP passage was detected between scRNA and PDGFR siRNA transfected cells (FIG. 7D). Protein expression of PDGFR-α and -β was below detection limit (FIG. 7E), further supporting the finding that PDGFR is not involved in the thrombin response.

Similarly, knock down of c-KIT with siRNA did not affect the thrombin response (FIG. 3D). To confirm the results of PDGFR and c-KIT knock down, HUVECs were pretreated with Tyrphostin AG1296, a pharmacological inhibitor of both PDGFR and c-KIT. Similar to combined knock down of PDGFR-α and -β, AG1296 improved basal barrier function, but did not inhibit the thrombin response (FIG. 7F). Altogether, these data indicate that neither inhibition of c-Abl, nor inhibition of PDGFR or c-KIT underlie the barrier protective effects of imatinib.

Example 5

The Tyrosine Kinase Arg is a Mediator of Thrombin-Induced Hyperpermeability

Figure 4A:
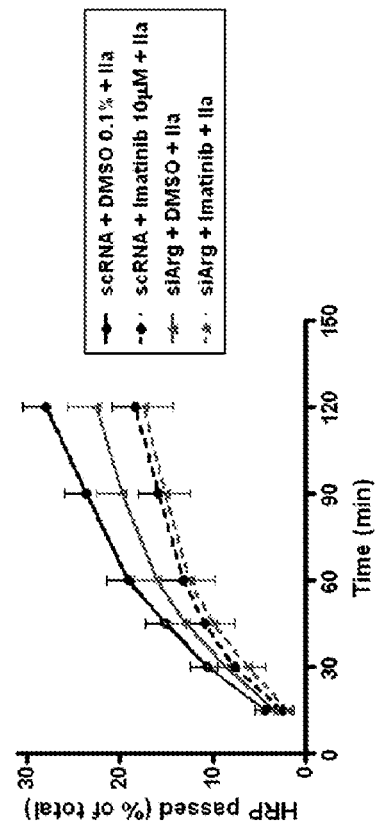
FIG. 4—Inhibition of Arg mimics the effects of imatinib during thrombin stimulation. HUVECs were transfected with siRNA against Arg, seeded on polycarbonate filters, ECIS gold electrodes or 5 cm² wells, and grown to confluence for 48 h (ECIS measurements and WesternBlot) or 120 h (HRP passage and WesternBlot). Confluent cells were pretreated with imatinib (10 µM), DMSO (0.1%) or 1% HSA/M199, and stimulated with thrombin (IIa, 1 U/mL) or vector. A) Time curve of HRP passage in scRNA or Arg siRNA transfected cells after stimulation with thrombin or vector. Mean±SEM of N=4 experiments. **P<0.01 compared to scRNA+IIa. B) Time curve of HRP passage in cells transfected with scRNA or Arg siRNA, pretreated with imatinib or DMSO, and subsequently stimulated with thrombin. Mean±SEM of N=4 experiments. scRNA+DMSO+IIa vs. siArg+DMSO+IIa, P<0.05; scRNA+DMSO+IIa vs. scRNA+Imatinib 10 µM+IIa, P<0.001; scRNA+DMSO+IIa vs. siArg+Imatinib 10 µM+IIa, P<0.001; siArg+DMSO+IIa vs. scRNA+Imatinib 10 µM+IIa, P<0.05; siArg+DMSO+IIa vs. siArg+Imatinib 10 µM+IIa, P<0.01 in Repeated Measures ANOVA. C) Normalized endothelial resistance during thrombin stimulation in HUVECs transfected with scRNA or Arg siRNA. Resistance was normalized to the moment just before thrombin stimulation. The thrombin response was quantified by calculating the maximal decrease in normalized resistance (insert). Mean±SEM of N=4 experiments. *P<0.05. D) Normalized resistance in cells transfected with scRNA or Arg siRNA, pretreated with imatinib or DMSO, and stimulated with thrombin. Mean±SEM of N=5 experiments. E) The thrombin response was quantified by calculating the maximal decrease in normalized resistance. Mean±SEM of N=5 experiments. *P<0.05, **P<0.01. F) Arg protein expression in scRNA or Arg siRNA transfected cells, lysated 48 h or 120 h after transfection (insert). Protein expression was quantified with a semi-quantitive method, and normalized for loading with β-actin. Mean of N=2 experiments.
Figure 4B:
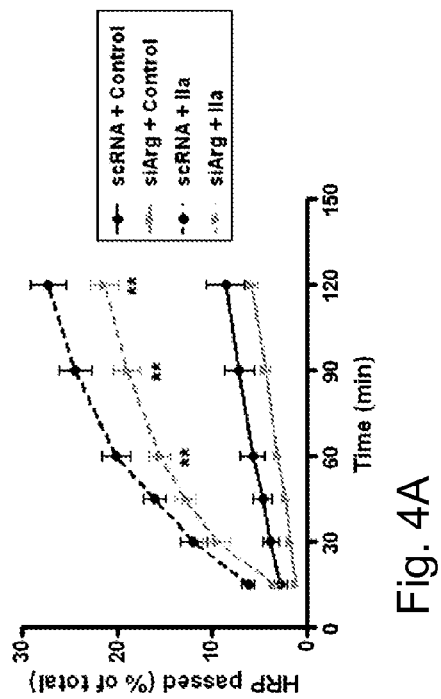
Figure 4D:
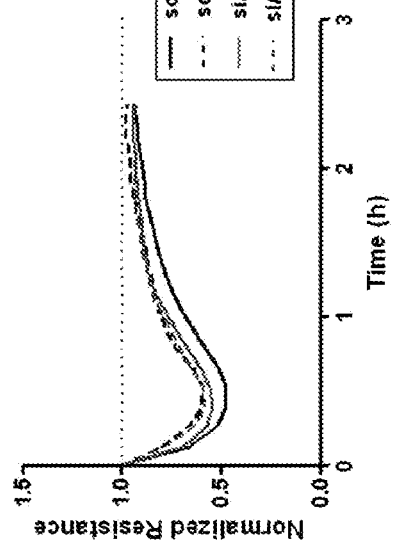
Figure 4C:
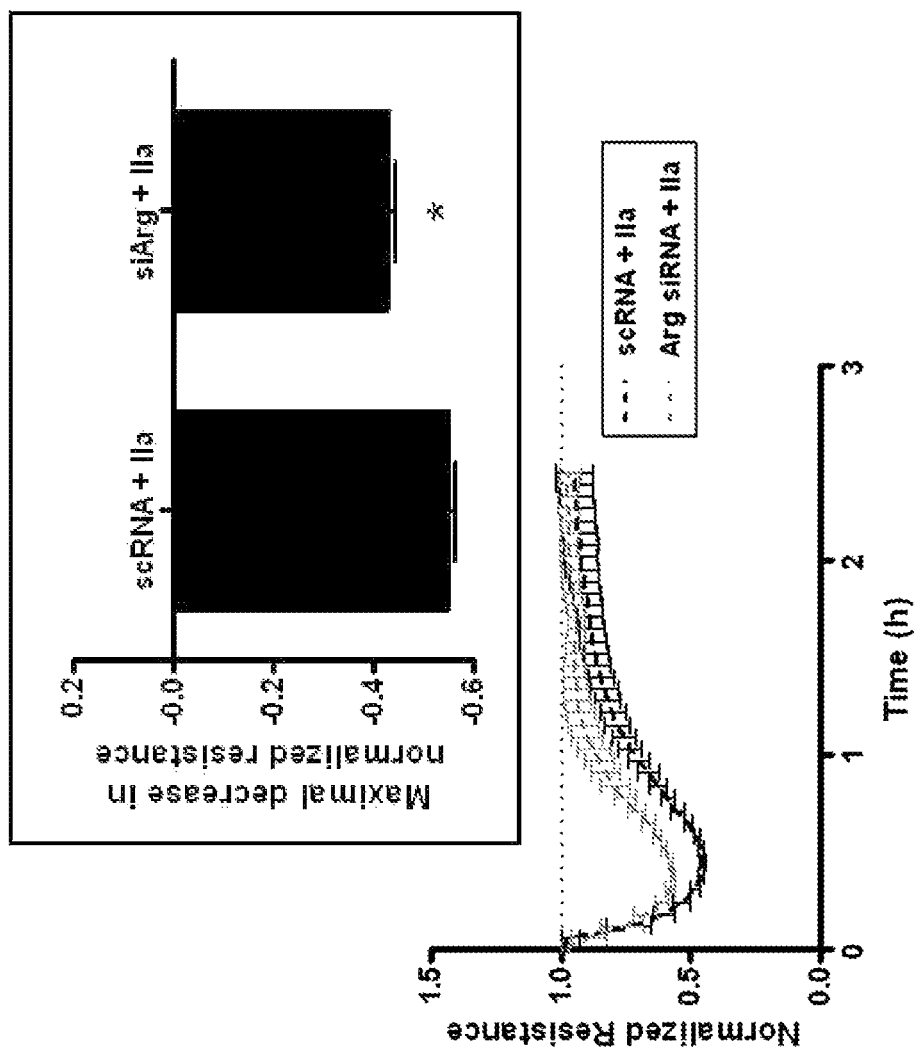
Figure 4F:
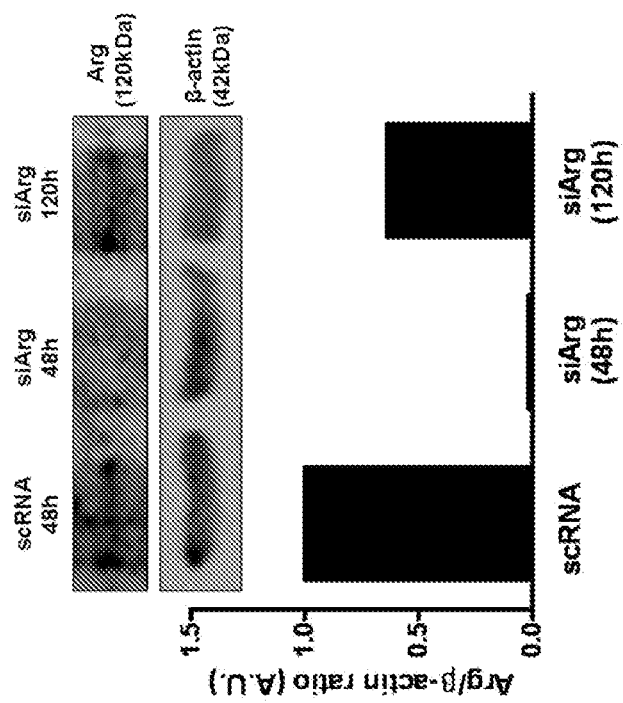
Figure 4E:
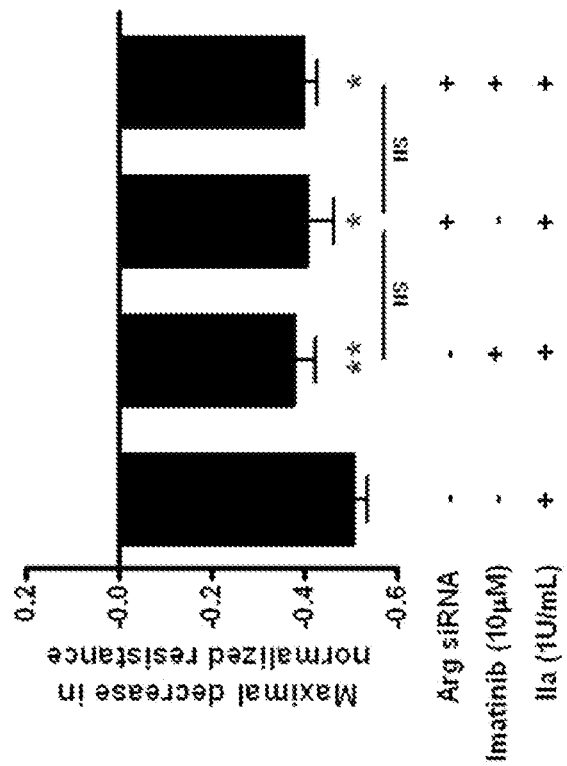

Finally, we investigated whether Arg is involved in thrombin-induced endothelial barrier dysfunction. Knock down of Arg significantly reduced the thombin-induced passage of HRP. The HRP passage was lower in Arg siRNA transfected cells compared to scRNA transfected cells (FIG. 4A; 15.5±1.1% vs. 20.1±1.5%, respectively, P<0.01 after 1 h and 21.3±1.5% vs. 27.3±1.8%, respectively, P<0.01 after 2 h). Imatinib pretreatment had an additive effect to Arg knock down on the thrombin response, as the passage of HRP was significantly lower in Arg deficient cells pretreated with imatinib, compared to Arg deficient cells pretreated with DMSO (FIG. 4B, P<0.01). In ECIS measurements Arg knock down attenuated the thrombin response as indicated by a lower drop in endothelial resistance and a faster recovery towards baseline values (FIG. 4C). Knock down of Arg mimicked pretreatment with imatinib, as a similar decrease in normalized resistance was observed in Arg deficient cells and cells pretreated with imatinib, while pretreatment with imatinib had no additive effect (FIGS. 4D and E). The efficiency of Arg knock down was higher after 48 h than after 120 h (FIG. 4F). As the interval between transfection and measurement differs for ECIS measurements (48 h) and HRP passage experiments (120 h), the difference in Arg knock down likely explains the observation that Arg knock down exactly mimicked imatinib in ECIS measurements, but not in HRP passage experiments.

These data indicate that imatinib attenuates thrombin-induced hyperpermeability through inhibition of Arg. Furthermore, these data identify Arg as a novel mediator of the thrombin response. Arg importantly contributes to thrombin-induced endothelial barrier dysfunction, as inhibition of Arg reduces the thrombin-induced macromolecule passage up to 40%.

Example 6

Treatment of Sepsis with ARG Inhibitor

Sepsis is diagnosed if two or more of the following criteria are present: abnormal body temperature (<36° C. or >38° C.), abnormal white blood cell counts (<4 or >12×109/L), a microbiologically proven or clinical source of infection, tachycardia (>90/min) and tachypnea (>20/min or a partial pressure of arterial carbon dioxide ($P_aCO_2$) <32 mmHg). Upon diagnosis of sepsis, imatinib treatment will be initiated at a dose of 400 mg daily, administered orally or intravenously. Indicators of clinical response are: presence of pulmonary edema on chest X-ray or CT, hemoglobin oxygen saturation, partial pressure of arterial oxygen ($P_aO_2$)/fraction of inspired oxygen ($F_iO_2$) ratio, ventilator dependency, vasopressor dependency and systemic blood pressure. If clinical response remains absent for 2 days, the imatinib dose can be increased to 400 mg twice daily. The maximal duration of treatment is 3 weeks.

Example 7

Treatment of Post-Radiation Pulmonary Edema with ARG Inhibitor

Severe pulmonary edema may follow radiotherapy, depending on the dose and duration of irradiation. Pulmonary edema upon irradiation is diagnosed by evidence for pulmonary edema on chest X-ray or CT of the thorax and hypoxemia. Upon diagnosis of post-radiation pulmonary edema imatinib treatment will be initiated with an initial dose of 400 mg daily administered orally or intravenously. Parameters for follow-up of pulmonary edema include: presence of pulmonary edema on chest X-ray or CT (thorax), arterial oxygen tension and hemoglobin oxygen saturation. If clinical response remains absent for 2 days, the imatinib dose can be increased to 400 mg twice daily. The maximal duration of treatment is exceed 3 weeks.

Example 8

Treatment of Reperfusion Pulmonary Edema after Pulmonary Endarterectomy with ARG Inhibitor Reperfusion pulmonary edema occurs usually occurs within 72 h after pulmonary endarterectomy (Levinson et al. J Thorac Cardiovasc Surg. 1990 April; 99(4):670-8; Levinson et al. Am Rev Respir Dis. 1986 December; 134(6):1241-5), and is diagnosed by presence of pulmonary edema on chest X-ray or CT (thorax), arterial oxygen tension and hemoglobin oxygen saturation. After performance of pulmonary endarterectomy, imatinib treatment will be initiated with an initial dose of 400 mg daily administered orally or intravenously to prevent development of pulmonary edema. Parameters for follow-up of pulmonary edema include: presence of pulmonary edema on chest X-ray or CT (thorax), arterial oxygen tension, hemoglobin oxygen saturation and ventilator dependency. If clinical response remains absent for 2 days, the imatinib dose can be increased to 400 mg twice daily. The maximal duration of treatment is 3 weeks.

Example 9

Treatment of No Reflow Stenosis with ARG Inhibitor

No reflow stenosis is a phenomen commonly observed during heart catheterization for stenosis of coronary arteries, which is likely caused by edema formation in the vascular wall surrounding the lesion. Imatinib treatment will be initiated 12 h (single dose of 400 mg administered orally or intravenously) before the start of heart catheterization to prevent development of edema in the vascular wall during the procedure and continued after the procedure (400 mg daily) to prevent edema formation in the postoperative phase. The maximal duration of treatment is 1 week.

Example 10

Treatment of Acute Lung Injury/Acute Respiratory Distress Syndrome (ALI/ARDS)

ALI/ARDS may develop as a consequence of pulmonary diseases (e.g. pneumonia, lung contusion or drowning), or as a consequence of systemic disease (e.g. sepsis). ALI and ARDS are diagnosed according to the American European Consensus Conference criteria. Upon diagnosis of ALI/ARDS, imatinib treatment will be initiated on top of regular treatment as indicated in guidelines on ALI/ARDS treatment. Starting dose of imatinib will be 400 mg daily, administered orally or intravenously. Indicators of clinical response are: presence of pulmonary edema on chest X-ray or CT, hemoglobin oxygen saturation, partial pressure of arterial oxygen ($P_aO_2$)/fraction of inspired oxygen ($F_iO_2$) ratio, ventilator dependency and extravascular lung water as measured by single indicator thermodilution technique. If clinical response remains absent for 2 days, the imatinib dose can be increased to 400 mg twice daily. The maximal duration of treatment is 3 weeks.

Materials & Methods
Reagents

Imatinib mesylate was purchased from ChemieTek (Indianapolis, Ind., USA) and dissolved in dimethylsulphoxide (DMSO) to a stock concentration of 10 mM. Tyrphostin AG1296 was purchased from Sigma Aldrich (Steinheim, Germany) and dissolved in DMSO to a stock concentration of 5 mM. Thrombin was purchased from Sigma Aldrich (Zwijndrecht, The Netherlands). Y-27632 was purchased from Tocris Cookson Ltd (London, UK). Small interference RNAs (siRNAs) against c-Abl, PDGFR-α and -β, Arg, c-KIT and scrambled RNAs (scRNA) were from Santa Cruz Biotechnology (Santa Cruz, Calif., USA). The following antibodies were used: anti c-Abl (#2862), anti PDGFR-α (#3174) and -β (#3169), all from Cell Signaling Technologies (Danvers, Mass., USA), anti β-actin (Sigma Aldrich), anti VE-cadherin (SC-6458, Santa Cruz) and Arg (SC-6356, Santa Cruz) and β-catenin (clone 8E7, Upstate/Millipore, Temecula, Calif., USA).

Cell Culture

For human umbilical vein endothelial cells (HUVECs), umbilical cords were obtained from the Amstelland Ziekenhuis, Amstelveen. Cells were isolated from healthy donors, and extensively characterized as previously described.[15] After isolation, cells were resuspended in M199 medium (Biowhittaker/Lonza, Verviers, Belgium), supplemented with penicilline 100 U/mL and streptomycin 100 mg/mL (Biowhittaker/Lonza, Verviers, Belgium), heat-inactivated human serum 10% (Sanquin CLB, Amsterdam, The Netherlands), heat-inactivated new-born calf serum 10% (Gibco, Grand Island, N.Y.), crude endothelial cell growth factor 150 µg/mL (prepared from bovine brains), L-glutamine 2 mmol/L (Biowhittaker/Lonza), and heparin 5 U/mL (Leo Pharmaceutical Products, Weesp, The Netherlands). Cells were cultured at 37° C. and 5% $CO_2$, with a change of culture medium every other day. Cells were cultured up to passage 2, for experiments passage 1-2 cells were used.

Human pulmonary microvascular cells were isolated from human lung tissue as previously described.[16] Cells were cultured in EGM2-MV culture medium (EBM2 medium supplemented with 5% foetal bovine serum, human epidermal growth factor, fibroblast growth factor, vascular endothelial growth factor, insulin-like growth factor, hydrocortisone, ascorbic acid, gentamicin and amphotericin according to the manufacturers protocol [BioWhittaker/Lonza], and with penicillin [100 U/mL] and streptomycin [100 mg/mL]) and seeded on gelatine-coated 25 cm² culture flasks. Cells were grown to confluence at 37 C. and 5% $CO_2$, with a change of culture medium every other day. They were extensively characterized as endothelial cells by the presence of endothelial markers and the absence of epithelial, lymphatic and smooth muscle cell markers. Cells were cultured up to passage 7, for experiments passage 4-7 cells were used. Human foreskin microvascular cells were isolated from human foreskin[7], and cultured with EGM2-MV culture medium. Cells were grown to confluence at 37° C. and 5% $CO_2$, with a change of culture medium every other day, and similarly characterized as endothelial cells.[17]

Isolation of Human Pulmonary Microvascular Endothelial Cells (HPMVEC)

Lung tissue was obtained from patients undergoing lobectomy for primary lung cancer or metastasis (Department of Thoracic Surgery, VU University Medical Centre, Amsterdam). After rinsing lung tissue in phosphate-buffered saline (PBS), pleural tissue was removed and the remaining tissue was minced during 5 minutes. The minced tissue was incubated in 20 mL 0.3% type II collagenase solution (Sigma, St. Louis, Mo., USA) in PBS during 60 min under gentle shaking. Digestion was stopped by addition of EGM2-MV culture medium (EBM2 medium supplemented with 5% fetal bovine serum, human epidermal growth factor, fibroblast growth factor, vascular endothelial growth factor, insulin-like growth factor, hydrocortisone, ascorbic acid according to the manufacturers protocol [Lonza, Basel, Switzerland], and with penicillin [100 U/mL] and streptomycin [100 mg/mL, Lonza, Biowhittaker, Verviers, Belgium]). After digestion, the suspension was flushed through a 100 µm and a 70 µm cell strainer (BD Biosciences, Bedford, USA). The filtered suspension was centrifuged for 5 min at 230× G/21° C., and the pellet resuspended in 120 µL EGM2-MV, 40 µL FcR blocking reagent and 40 µL CD31-coated magnetic beads (Miltenyi Biotec GmbH, Bergisch Gladbach, Germany) and incubated for 15 min at 4° C. CD31+ endothelial cells were separated from other cells by passing the cell suspension through a magnetic field. Freshly isolated endothelial cells were seeded in gelatin- and fibronectin-coated 25 cm2 culture flasks. After 7-10 days of culture, cells were further purified by repeating the magnetic bead procedure until a 95-100% pure culture was reached. Cells were extensively characterized as endothelial cells by the presence of endothelial markers (CD31, VE-cadherin, vWF, Tie2 and Ulex lectin binding), and the absence of epithelial cell (pancytokeratin), vascular smooth muscle cell (smooth muscle α-actin) or lymphatic markers (LYVE-1). Cells were further characterized as microvascular encothelial cells (Ulex lectin).

Endothelial Barrier Function

Endothelial barrier function was evaluated with horse radish peroxidase (HRP) passage and Electrical Cell-substrate Impedance Sensing (ECIS). For measurement of HRP passage, confluent cells were seeded in 1:1 density on 0.33 cm$^2$ Costar polycarbonate filters, pore-size 3.0 μm (Corning, Lowell, Mass., USA) and grown to confluence in 4 or 5 days, with change of culture medium every other day. For pretreatment, pharmacological inhibitors or vector were dissolved in M199 supplemented with 1% human serum albumin (HSA, Sanquin CLB), and after removal of culture medium, solutions were added to the upper compartment of the filters during 60 min. For stimulation, pretreatment medium was changed for 1% HSA/M199 containing designated inhibitors, HRP 5 μg/mL (Sigma Aldrich) and thrombin 1 U/mL. 1% HSA/M199 was added to the lower compartment. At indicated time points samples were taken from the lower compartment; HRP concentration in samples was detected by measuring chemoluminiscence after addition of TMB/E (Upstate/Millipore).

For ECIS measurements, cells were trypsinized and seeded in 1:1 density on gelatine-coated ECIS arrays, each containing 8 wells with 10 gold electrodes/well (8 W10E, Applied Biophysics, Troy, N.Y., USA). Culture medium was refreshed 24 h after seeding, while experiments were performed 48 h after seeding. For pretreatment, designated pharmacological inhibitors or vector were dissolved in M199 supplemented with 1% HSA. After 90 min of pretreatment, thrombin was added directly to the cells for a final concentration of 1 U/mL. During stimulation impedance was measured at multiple frequencies to allow for calculation of resistance attributable to cell-cell adhesion (Rb) and resistance attributable to cell-matrix interaction (alpha). The absolute resistance was measured, while the relative resistance was calculated by normalization to the time point just before addition of the thrombin, to correct for baseline differences.

Immunofluorescence Staining

Cells were seeded on glass coverslips coated with gelatine 1% and pretreated with glutaraldehyde 0.5% (Fluka, St. Gallen, Switzerland). Cells were seeded in 1:1 density and grown to confluence in 48-72 hours. For pretreatment, culture medium was changed to 1% HSA/M199, containing pharmacological inhibitors or vector. After 60 min of pretreatment, thrombin was added directly to the wells for a final concentration of 1 U/mL. At indicated time points, medium was removed and warm paraformaldehyde 2% (Sigma Aldrich) was added to the cells, while kept on ice for 15 min. Cells were permeabilized with Triton X-100 0.05% (Sigma Aldrich) in phosphate-buffered saline (PBS), and incubated overnight with primary antibodies for β-catenin (1:100), VE-cadherin (1:400) or Arg (1:150) in 0.1% HSA/PBS. Subsequently, cells were washed and incubated with FITC-labeled secondary antibodies (Invitrogen, Paisly, United Kingdom) and rhodamine/phalloidin (Invitrogen) for 1 h at room temperature. Cells were washed and sealed in Vectashield mounting medium containing DAPI (Vector Laboratories Inc., Burlingham, Calif., USA) for nuclear staining. Immunofluorescent imaging was performed with an Axiovert 200 Marianas™ inverted wide-field fluorescence microscope, using a 40× Zeiss air lens (NA 0.75) and a 63× Zeiss oil lens (NA 1.4). All images were worked out with Slidebook software (Intelligent Imaging Innovation, Denver, Colo., USA).

RhoA Activity Assay

For analysis of RhoA activity, 10 cm$^2$ confluent cells/condition were pretreated with imatinib (10 μM) or vector (DMSO 0.1%) and stimulated with thrombin (1 U/mL) during indicated intervals. After stimulation, cells were washed with ice-cold PBS and lysed with lysis buffer containing 0.02 mM Tris/HCl pH 8.0, 0.15M NaCl, 0.09M KCl, 2 mM EDTA/NaOH pH 8.0, 5% Igepal, and 0.5% Triton X-100, further supplemented with PhosStop protease inhibitor (Roche Diagnostics, Mannheim, Germany), and Complete EDTA-free phosphatase inhibitor (Roche Diagnostics). After centrifugation of the cell lysates, the supernatant was snap-frozen and stored at −80° C. Relative RhoA activity was determined with a G-LISA RhoA Activity Assay (Cytoskeleton Inc, Denver, Colo., USA), according to the manufacturers protocol.

Transfections

Cells were transfected with Amaxa Technology (Amaxa Biosystems, Lonza), according to the manufacturers protocol. 80-90% confluent cells (passage 1) were trypsinized and transfected with indicated siRNAs (0.05 nmol for 10 cm$^2$ cells) according to the manufacturers protocol. After transfection, cells were seeded on gelatine-coated ECIS arrays or 5 cm$^2$ culture wells. For control of protein expression in transfected cells, 5 cm$^2$ confluent cells/condition where lysed 48 h or 120 h after transfection. 20 μg of total protein/condition was electrophoresed, transferred to nitrocellulose membranes and immunoblotted for c-Abl (1:1000, overnight at 4° C.), PDGFR-α and -β (both 1:200, overnight at 4° C.), and Arg (1:150, overnight at 4° C.). β-actin (1:100000) served as loading control.

Statistical Analyses

All data are reported as Mean±Standard Error of the Mean (SEM). N refers to the number of independent experiments. For comparison of 2 groups a Students t-test was used, for comparison of >2 groups an one-way ANOVA with Tukey post-hoc test was used. A P-value <0.05 was considered significant.

The invention claimed is:

1. A method of treating an individual suffering from or at risk of suffering from inflammatory edema, the method comprising:

administering an inhibitor of Abl-related gene (ARG) function to the individual thereby treating said edema in the individual, wherein the inhibitor inhibits or alters the ARG gene, ARG mRNA, or ARG protein.

2. A method according to claim 1 wherein said inflammatory edema is thrombin-induced edema.

3. The method according to claim 1, wherein the individual is suffering from sepsis, ALI/ARDS, preeclampsia, no reflow stenosis, pulmonary edema, post-radiation pulmonary edema, or post-endarteriectomy pulmonary edema.

4. A method for inhibiting endothelial barrier dysfunction in a collection of endothelial cells comprising an endothelial barrier that dysfunctions or is at risk of dysfunction, said method comprising:

providing said collection of endothelial cells with an inhibitor of Abl-related gene (ARG) function, thereby inhibiting endothelial barrier dysfunction in the collection of endothelial cells,
    wherein the inhibitor inhibits or alters the ARG gene, ARG mRNA, or ARG protein.

5. A method of treating an individual suffering from or at risk of suffering from inflammatory edema, the method comprising:
    administering an inhibitor of Abl-related gene (ARG) function to the individual thereby treating the edema in the individual,
    wherein the inhibitor inhibits alters the ARG gene, ARG mRNA, or ARG protein, and
    wherein said inhibitor of Abl-related gene (ARG) function comprises an inhibitor of tyrosine kinase activity of the protein encoded by said Abl-related gene (ARG).

6. A method according to claim 5, wherein said tyrosine kinase activity inhibitor specifically inhibits the tyrosine kinase activity of the protein encoded by said Abl-related gene (ARG).

7. The method according to claim 5, wherein said tyrosine kinase activity inhibitor does not significantly inhibit the tyrosine kinase activity of C-kit, PDGFR-alpha, and/or C-Abl.

8. The method according to claim 1, wherein said inhibitor of Abl-related gene (ARG) function comprises an antisense oligonucleotide specific for a pre-mRNA encoded by said Abl-related gene (ARG).

9. The method according to claim 1, wherein said inhibitor of Abl-related gene (ARG) function comprises an siRNA specific for mRNA encoded by said Abl-related gene (ARG).

10. The method according to claim 1, wherein said inhibitor of Abl-related gene (ARG) function is administered for a time period of between 1-20 weeks.

11. The method according to claim 10, wherein said inhibitor of Abl-related gene (ARG) function is administered to the individual for a time period of between 1-12 weeks.

12. A method of treating an individual diagnosed as suffering from or at risk of suffering from inflammatory edema, the method comprising:
    administering an inhibitor of Abl-related gene (ARG) function to the individual thereby treating the edema in the individual,
    wherein the inhibitor inhibits or alters the ARG gene, ARG mRNA, or ARG protein.

13. The method according to claim 12, wherein the inhibitor is administered for a time period of between 1-20 weeks.

14. A method for inhibiting endothelial barrier dysfunction in a collection of endothelial cells comprising an endothelial barrier that dysfunctions or is at risk of dysfunction, the method comprising:
    contacting the collection of endothelial cells with an inhibitor of Abl-related gene (ARG) function, thereby inhibiting endothelial barrier dysfunction in the collection of endothelial cells,
    wherein the inhibitor inhibits or alters the ARG gene, ARG mRNA, or ARG protein, and
    wherein the inhibitor of ARG function comprises an inhibitor of tyrosine kinase activity of the protein encoded by ARG.

15. The method according to claim 14, wherein the tyrosine kinase activity inhibitor specifically inhibits the tyrosine kinase activity of the protein encoded by ARG.

16. The method according to claim 14, wherein the tyrosine kinase activity inhibitor does not significantly inhibit the tyrosine kinase activity of C-kit, PDGFR-alpha, and/or C-Abl.

17. The method according to claim 4, wherein the inhibitor of ARG function comprises an antisense oligonucleotide specific for a pre-mRNA encoded by ARG.

18. The method according to claim 4, wherein the inhibitor of ARG function comprises an siRNA specific for mRNA encoded by ARG.

19. The method according to claim 4, wherein the inhibitor of ARG function is provided for between 1 and 20 weeks.

20. The method according to claim 19, wherein the inhibitor of ARG function is provided for between 1 and 12 weeks.

21. The method according to claim 1, wherein the inhibitor of ARG function is imatinib or a pharmaceutically acceptable salt thereof.

22. The method according to claim 4, wherein the inhibitor of ARG function is imatinib or a pharmaceutically acceptable salt thereof.

23. The method according to claim 12, wherein the inhibitor of ARG function is imatinib or a pharmaceutically acceptable salt thereof.

* * * * *

SEQUENCE LISTING

```
<160> NUMBER OF SEQ ID NOS: 1

<210> SEQ ID NO 1
<211> LENGTH: 1182
<212> TYPE: PRT
<213> ORGANISM: Homo sapiens

<400> SEQUENCE: 1

Met Gly Gln Gln Val Gly Arg Val Gly Glu Ala Pro Gly Leu Gln Gln
```

```
  1               5                   10                  15
Pro Gln Pro Arg Gly Ile Arg Gly Ser Ser Ala Ala Arg Pro Ser Gly
                 20                  25                  30

Arg Arg Arg Asp Pro Ala Gly Arg Thr Thr Glu Thr Gly Phe Asn Ile
                 35                  40                  45

Phe Thr Gln His Asp His Phe Ala Ser Cys Val Glu Asp Gly Phe Glu
                 50                  55                  60

Gly Asp Lys Thr Gly Gly Ser Ser Pro Glu Ala Leu His Arg Pro Tyr
 65                  70                  75                  80

Gly Cys Asp Val Glu Pro Gln Ala Leu Asn Glu Ala Ile Arg Trp Ser
                 85                  90                  95

Ser Lys Glu Asn Leu Leu Gly Ala Thr Glu Ser Asp Pro Asn Leu Phe
                100                 105                 110

Val Ala Leu Tyr Asp Phe Val Ala Ser Gly Asp Asn Thr Leu Ser Ile
                115                 120                 125

Thr Lys Gly Glu Lys Leu Arg Val Leu Gly Tyr Asn Gln Asn Gly Glu
                130                 135                 140

Trp Ser Glu Val Arg Ser Lys Asn Gly Gln Gly Trp Val Pro Ser Asn
145                 150                 155                 160

Tyr Ile Thr Pro Val Asn Ser Leu Glu Lys His Ser Trp Tyr His Gly
                165                 170                 175

Pro Val Ser Arg Ser Ala Ala Glu Tyr Leu Leu Ser Ser Leu Ile Asn
                180                 185                 190

Gly Ser Phe Leu Val Arg Glu Ser Glu Ser Ser Pro Gly Gln Leu Ser
                195                 200                 205

Ile Ser Leu Arg Tyr Glu Gly Arg Val Tyr His Tyr Arg Ile Asn Thr
                210                 215                 220

Thr Ala Asp Gly Lys Val Tyr Val Thr Ala Glu Ser Arg Phe Ser Thr
225                 230                 235                 240

Leu Ala Glu Leu Val His His Ser Thr Val Ala Asp Gly Leu Val
                245                 250                 255

Thr Thr Leu His Tyr Pro Ala Pro Lys Cys Asn Lys Pro Thr Val Tyr
                260                 265                 270

Gly Val Ser Pro Ile His Asp Lys Trp Glu Met Glu Arg Thr Asp Ile
                275                 280                 285

Thr Met Lys His Lys Leu Gly Gly Gly Gln Tyr Gly Glu Val Tyr Val
                290                 295                 300

Gly Val Trp Lys Lys Tyr Ser Leu Thr Val Ala Val Lys Thr Leu Lys
305                 310                 315                 320

Glu Asp Thr Met Glu Val Glu Glu Phe Leu Lys Glu Ala Ala Val Met
                325                 330                 335

Lys Glu Ile Lys His Pro Asn Leu Val Gln Leu Leu Gly Val Cys Thr
                340                 345                 350

Leu Glu Pro Pro Phe Tyr Ile Val Thr Glu Tyr Met Pro Tyr Gly Asn
                355                 360                 365

Leu Leu Asp Tyr Leu Arg Glu Cys Asn Arg Glu Glu Val Thr Ala Val
                370                 375                 380

Val Leu Leu Tyr Met Ala Thr Gln Ile Ser Ser Ala Met Glu Tyr Leu
385                 390                 395                 400

Glu Lys Lys Asn Phe Ile His Arg Asp Leu Ala Ala Arg Asn Cys Leu
                405                 410                 415

Val Gly Glu Asn His Val Val Lys Val Ala Asp Phe Gly Leu Ser Arg
                420                 425                 430
```

```
Leu Met Thr Gly Asp Thr Tyr Thr Ala His Ala Gly Ala Lys Phe Pro
        435                 440                 445

Ile Lys Trp Thr Ala Pro Glu Ser Leu Ala Tyr Asn Thr Phe Ser Ile
450                 455                 460

Lys Ser Asp Val Trp Ala Phe Gly Val Leu Leu Trp Glu Ile Ala Thr
465                 470                 475                 480

Tyr Gly Met Ser Pro Tyr Pro Gly Ile Asp Leu Ser Gln Val Tyr Asp
                485                 490                 495

Leu Leu Glu Lys Gly Tyr Arg Met Glu Gln Pro Glu Gly Cys Pro Pro
            500                 505                 510

Lys Val Tyr Glu Leu Met Arg Ala Cys Trp Lys Trp Ser Pro Ala Asp
        515                 520                 525

Arg Pro Ser Phe Ala Glu Thr His Gln Ala Phe Glu Thr Met Phe His
530                 535                 540

Asp Ser Ser Ile Ser Glu Glu Val Ala Glu Glu Leu Gly Arg Ala Ala
545                 550                 555                 560

Ser Ser Ser Ser Val Val Pro Tyr Leu Pro Arg Leu Pro Ile Leu Pro
                565                 570                 575

Ser Lys Thr Arg Thr Leu Lys Lys Gln Val Glu Asn Lys Glu Asn Ile
            580                 585                 590

Glu Gly Ala Gln Asp Ala Thr Glu Asn Ser Ala Ser Ser Leu Ala Pro
        595                 600                 605

Gly Phe Ile Arg Gly Ala Gln Ala Ser Ser Gly Ser Pro Ala Leu Pro
    610                 615                 620

Arg Lys Gln Arg Asp Lys Ser Pro Ser Ser Leu Leu Glu Asp Ala Lys
625                 630                 635                 640

Glu Thr Cys Phe Thr Arg Asp Arg Lys Gly Gly Phe Phe Ser Ser Phe
                645                 650                 655

Met Lys Lys Arg Asn Ala Pro Thr Pro Pro Lys Arg Ser Ser Ser Phe
            660                 665                 670

Arg Glu Met Glu Asn Gln Pro His Lys Lys Tyr Glu Leu Thr Gly Asn
        675                 680                 685

Phe Ser Ser Val Ala Ser Leu Gln His Ala Asp Gly Phe Ser Phe Thr
    690                 695                 700

Pro Ala Gln Gln Glu Ala Asn Leu Val Pro Pro Lys Cys Tyr Gly Gly
705                 710                 715                 720

Ser Phe Ala Gln Arg Asn Leu Cys Asn Asp Asp Gly Gly Gly Gly Gly
                725                 730                 735

Gly Ser Gly Thr Ala Gly Gly Gly Trp Ser Gly Ile Thr Gly Phe Phe
            740                 745                 750

Thr Pro Arg Leu Ile Lys Lys Thr Leu Gly Leu Arg Ala Gly Lys Pro
        755                 760                 765

Thr Ala Ser Asp Asp Thr Ser Lys Pro Phe Pro Arg Ser Asn Ser Thr
770                 775                 780

Ser Ser Met Ser Ser Gly Leu Pro Glu Gln Asp Arg Met Ala Met Thr
785                 790                 795                 800

Leu Pro Arg Asn Cys Gln Arg Ser Lys Leu Gln Leu Glu Arg Thr Val
                805                 810                 815

Ser Thr Ser Ser Gln Pro Glu Glu Asn Val Asp Arg Ala Asn Asp Met
            820                 825                 830

Leu Pro Lys Lys Ser Glu Glu Ser Ala Ala Pro Ser Arg Glu Arg Pro
        835                 840                 845
```

-continued

```
Lys Ala Lys Leu Leu Pro Arg Gly Ala Thr Ala Leu Pro Leu Arg Thr
    850             855             860
Pro Ser Gly Asp Leu Ala Ile Thr Glu Lys Asp Pro Pro Gly Val Gly
865             870             875             880
Val Ala Gly Val Ala Ala Ala Pro Lys Gly Lys Glu Lys Asn Gly Gly
                885             890             895
Ala Arg Leu Gly Met Ala Gly Val Pro Glu Asp Gly Glu Gln Pro Gly
            900             905             910
Trp Pro Ser Pro Ala Lys Ala Ala Pro Val Leu Pro Thr Thr His Asn
        915             920             925
His Lys Val Pro Val Leu Ile Ser Pro Thr Leu Lys His Thr Pro Ala
    930             935             940
Asp Val Gln Leu Ile Gly Thr Asp Ser Gln Gly Asn Lys Phe Lys Leu
945             950             955             960
Leu Ser Glu His Gln Val Thr Ser Ser Gly Asp Lys Asp Arg Pro Arg
                965             970             975
Arg Val Lys Pro Lys Cys Ala Pro Pro Pro Pro Val Met Arg Leu
            980             985             990
Leu Gln His Pro Ser Ile Cys Ser Asp Pro Thr Glu Glu Pro Thr Ala
        995             1000            1005
Leu Thr Ala Gly Gln Ser Thr Ser Glu Thr Gln Glu Gly Gly Lys
    1010            1015            1020
Lys Ala Ala Leu Gly Ala Val Pro Ile Ser Gly Lys Ala Gly Arg
    1025            1030            1035
Pro Val Met Pro Pro Pro Gln Val Pro Leu Pro Thr Ser Ser Ile
    1040            1045            1050
Ser Pro Ala Lys Met Ala Asn Gly Thr Ala Gly Thr Lys Val Ala
    1055            1060            1065
Leu Arg Lys Thr Lys Gln Ala Ala Glu Lys Ile Ser Ala Asp Lys
    1070            1075            1080
Ile Ser Lys Glu Ala Leu Leu Glu Cys Ala Asp Leu Leu Ser Ser
    1085            1090            1095
Ala Leu Thr Glu Pro Val Pro Asn Ser Gln Leu Val Asp Thr Gly
    1100            1105            1110
His Gln Leu Leu Asp Tyr Cys Ser Gly Tyr Val Asp Cys Ile Pro
    1115            1120            1125
Gln Thr Arg Asn Lys Phe Ala Phe Arg Glu Ala Val Ser Lys Leu
    1130            1135            1140
Glu Leu Ser Leu Gln Glu Leu Gln Val Ser Ser Ala Ala Ala Gly
    1145            1150            1155
Val Pro Gly Thr Asn Pro Val Leu Asn Asn Leu Leu Ser Cys Val
    1160            1165            1170
Gln Glu Ile Ser Asp Val Val Gln Arg
    1175            1180
```